US010219798B2

(12) United States Patent
Capote

(10) Patent No.: US 10,219,798 B2
(45) Date of Patent: Mar. 5, 2019

(54) SURGICAL INSTRUMENT AND METHOD OF USE

(71) Applicant: Warsaw Orthopedic, Inc., Warsaw, IN (US)

(72) Inventor: Cristian A. Capote, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 585 days.

(21) Appl. No.: 14/800,302

(22) Filed: Jul. 15, 2015

(65) Prior Publication Data

US 2017/0014117 A1  Jan. 19, 2017

(51) Int. Cl.
*A61B 17/02* (2006.01)
*A61B 90/57* (2016.01)
*A61B 90/50* (2016.01)

(52) U.S. Cl.
CPC ...... *A61B 17/0206* (2013.01); *A61B 17/0293* (2013.01); *A61B 90/57* (2016.02); *A61B 2090/508* (2016.02); *A61B 2090/571* (2016.02)

(58) Field of Classification Search
CPC ............. A61B 17/0206; A61B 17/025; A61B 17/0293; A61B 90/50; A61B 2090/506; A61B 2090/508; A61B 2090/57; A61B 2090/571
USPC ........ 600/214, 215, 222, 227, 228–231, 234
See application file for complete search history.

(56) References Cited

U.S. PATENT DOCUMENTS

| 2,693,795 | A | 11/1954 | Greishaber |
| 3,626,471 | A | 12/1971 | Florin |
| 3,965,890 | A | 6/1976 | Gauthier |
| 5,027,793 | A | 7/1991 | Englehardt et al. |
| 6,074,343 | A | 6/2000 | Nathanson et al. |
| 6,206,826 | B1 | 3/2001 | Mathews et al. |
| 6,322,500 | B1 * | 11/2001 | Sikora ............... A61B 17/0206 600/219 |
| 6,416,469 | B1 | 7/2002 | Phung et al. |
| 6,599,240 | B2 | 7/2003 | Puchovsky et al. |
| 7,207,949 | B2 | 4/2007 | Miles et al. |
| 7,537,565 | B2 | 5/2009 | Bass |
| 7,582,058 | B1 | 9/2009 | Miles et al. |
| 7,585,001 | B2 * | 9/2009 | Rose .................... F16L 37/086 285/305 |
| 7,691,057 | B2 | 4/2010 | Miles et al. |
| 7,785,253 | B1 | 8/2010 | Arambula et al. |
| 7,892,173 | B2 | 2/2011 | Miles et al. |
| 7,905,840 | B2 | 3/2011 | Pimenta et al. |

(Continued)

FOREIGN PATENT DOCUMENTS

WO   2015054070 A1   4/2015

*Primary Examiner* — Anu Ramana

(57) ABSTRACT

A surgical instrument comprises an element connectable with a fixture. A first member is independently and selectively movable relative to the element and includes a part engageable with tissue of a substantially posterior portion of an incision relative to a body. A second member is independently and selectively movable relative to the element and includes a part engageable with tissue of a substantially anterior portion of the incision relative to the body. A third member is independently and selectively movable relative to the element and includes a part engageable with tissue of a substantially cephalad portion of the incision relative to the body. Systems and methods are disclosed.

20 Claims, 14 Drawing Sheets

(56) References Cited

U.S. PATENT DOCUMENTS

| | | | |
|---|---|---|---|
| 7,920,922 B2 | 4/2011 | Gharib et al. |
| 7,935,051 B2 | 5/2011 | Miles et al. |
| 7,962,191 B2 | 6/2011 | Marino et al. |
| 8,000,782 B2 | 8/2011 | Gharib et al. |
| 8,005,535 B2 | 8/2011 | Gharib et al. |
| 8,016,767 B2 | 9/2011 | Miles et al. |
| 8,038,611 B2 | 10/2011 | Douglas et al. |
| 8,055,349 B2 | 11/2011 | Gharib et al. |
| 8,062,218 B2 | 11/2011 | Sebastian et al. |
| D652,519 S | 1/2012 | Miles et al. |
| D652,921 S | 1/2012 | Miles et al. |
| D652,922 S | 1/2012 | Miles et al. |
| 8,114,019 B2 | 2/2012 | Miles et al. |
| 8,133,173 B2 | 3/2012 | Miles et al. |
| 8,137,284 B2 | 3/2012 | Miles et al. |
| 8,165,653 B2 | 4/2012 | Marino et al. |
| 8,172,750 B2 | 5/2012 | Miles et al. |
| 8,182,423 B2 | 5/2012 | Miles et al. |
| 8,187,179 B2 | 5/2012 | Miles et al. |
| 8,192,356 B2 | 6/2012 | Miles et al. |
| 8,192,357 B2 | 6/2012 | Miles et al. |
| D666,292 S | 8/2012 | Miles et al. |
| D666,294 S | 8/2012 | Miles et al. |
| 8,244,343 B2 | 8/2012 | Gharib et al. |
| D666,923 S | 9/2012 | Buffington et al. |
| 8,303,498 B2 | 11/2012 | Miles et al. |
| 8,343,046 B2 | 1/2013 | Miles et al. |
| 8,353,826 B2 | 1/2013 | Weiman |
| 8,357,184 B2 | 1/2013 | Woolley et al. |
| 8,535,320 B2 | 9/2013 | Woolley et al. |
| 8,636,655 B1 | 1/2014 | Childs |
| 8,882,662 B2 | 11/2014 | Charles |
| 9,044,280 B1 | 6/2015 | Arambula et al. |
| 9,078,635 B2 * | 7/2015 | Menendez ............ A61B 17/02 |
| 2006/0224044 A1 | 10/2006 | Marchek et al. |
| 2007/0208227 A1 | 9/2007 | Smith et al. |
| 2011/0046448 A1 | 2/2011 | Paolitto et al. |
| 2012/0245431 A1 | 9/2012 | Baudouin et al. |
| 2012/0283521 A1 | 11/2012 | Smith et al. |
| 2013/0190575 A1 | 7/2013 | Mast et al. |
| 2014/0135584 A1 | 5/2014 | Lee et al. |
| 2015/0088030 A1 | 3/2015 | Taylor |
| 2015/0100129 A1 | 4/2015 | Waugh et al. |

\* cited by examiner

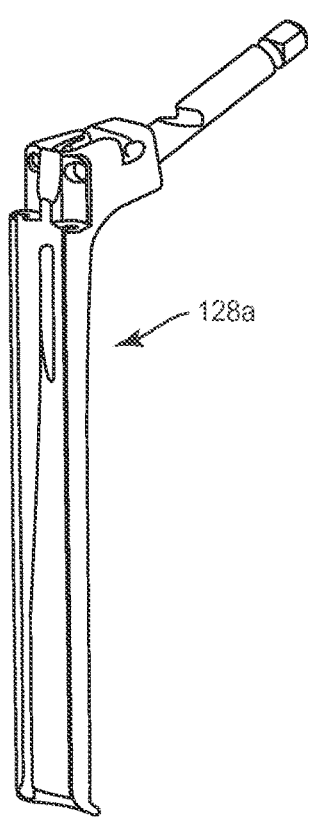
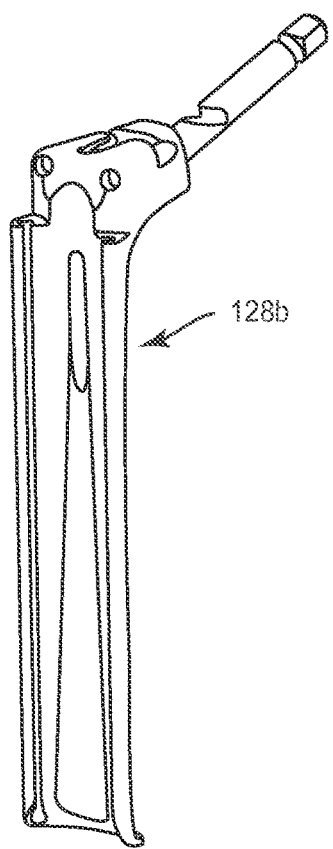
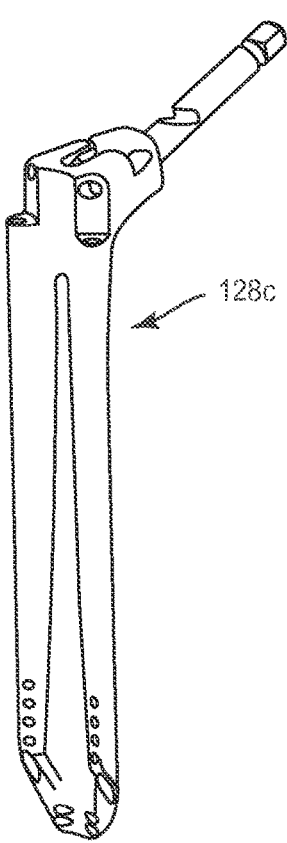
FIG. 2a                FIG. 2b                FIG. 2c
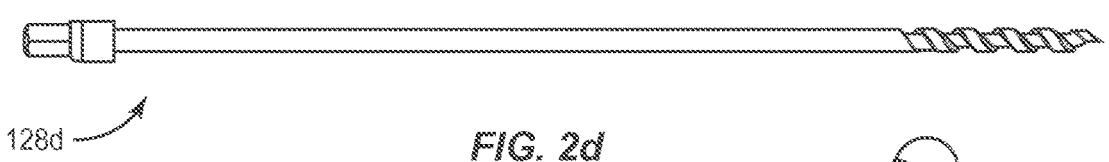
FIG. 2d
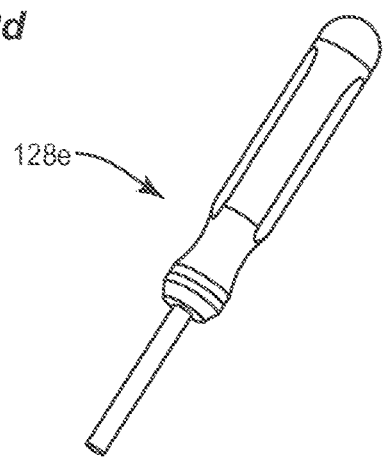
FIG. 2e

SURGICAL INSTRUMENT AND METHOD OF USE

TECHNICAL FIELD

The present disclosure generally relates to medical devices for the treatment of musculoskeletal disorders, and more particularly to a spinal implant system and a method for treating a spine, which employ an oblique pathway suitable for accessing disc spaces in the lower lumbar region, for example, an L5-S1 disc space.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, laminectomy and implantable prosthetics. As part of these surgical treatments, spinal constructs, such as, for example, bone fasteners, spinal rods and interbody devices can be used to provide stability to a treated region. For example, during surgical treatment, surgical instruments can be used to deliver components of the spinal constructs to the surgical site for fixation with bone to immobilize a joint. This disclosure describes an improvement over these prior technologies.

SUMMARY

In some embodiments, a surgical instrument is provided that comprises an element connectable with a fixture. A first member is independently and selectively movable relative to the element and includes a part engageable with tissue of a substantially posterior portion of an incision relative to a body. A second member is independently and selectively movable relative to the element and includes a part engageable with tissue of a substantially anterior portion of the incision relative to the body. A third member is independently and selectively movable relative to the element and includes a part engageable with tissue of a substantially cephalad portion of the incision relative to the body. Systems and methods of use for accessing lumbar disc spaces via an oblique lateral approach are provided.

BRIEF DESCRIPTION OF THE DRAWINGS

The present disclosure will become more readily apparent from the specific description accompanied by the following drawings, in which:

FIGS. 2a-2e are perspective views of embodiments of components of a surgical system in accordance with the principles of the present disclosure;

DETAILED DESCRIPTION

Figure 1:
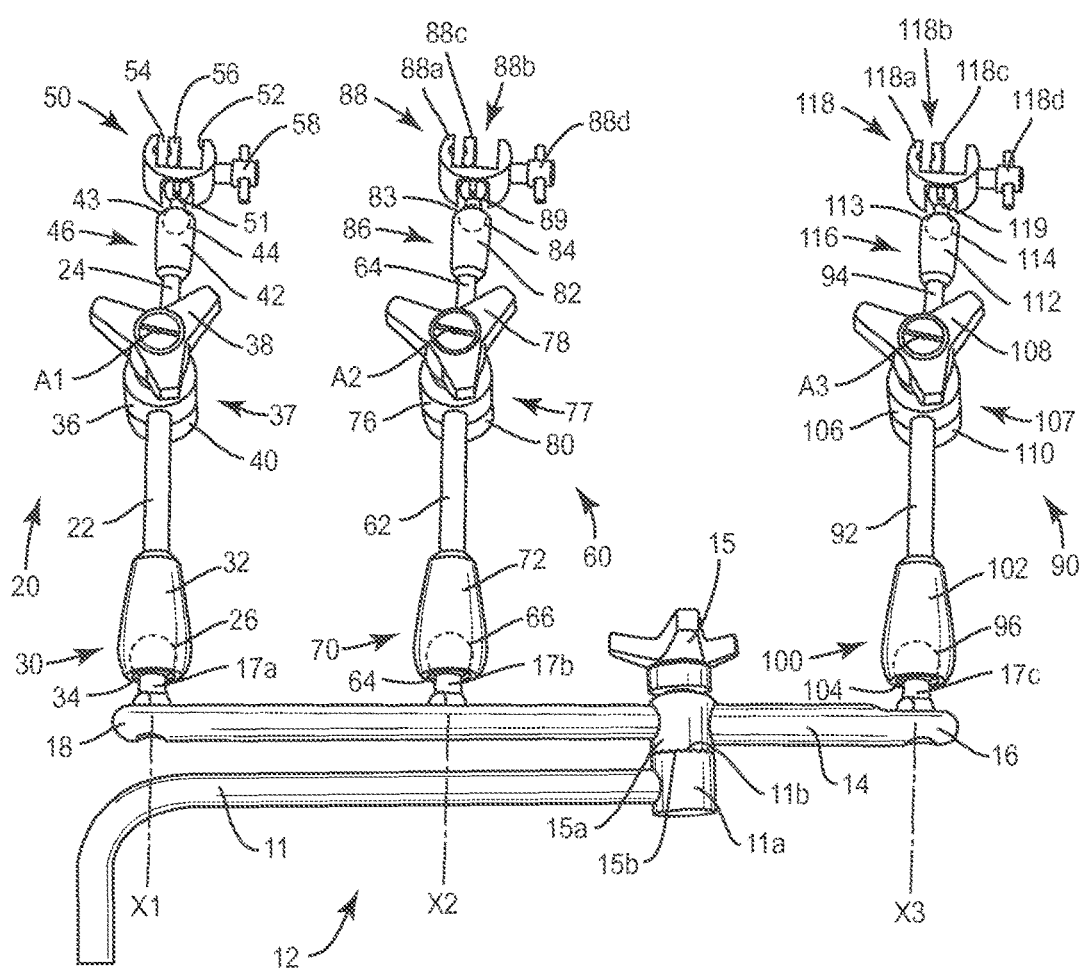
FIG. 1 is a perspective view of components of one embodiment of a surgical system in accordance with the principles of the present disclosure.
Figure 3:
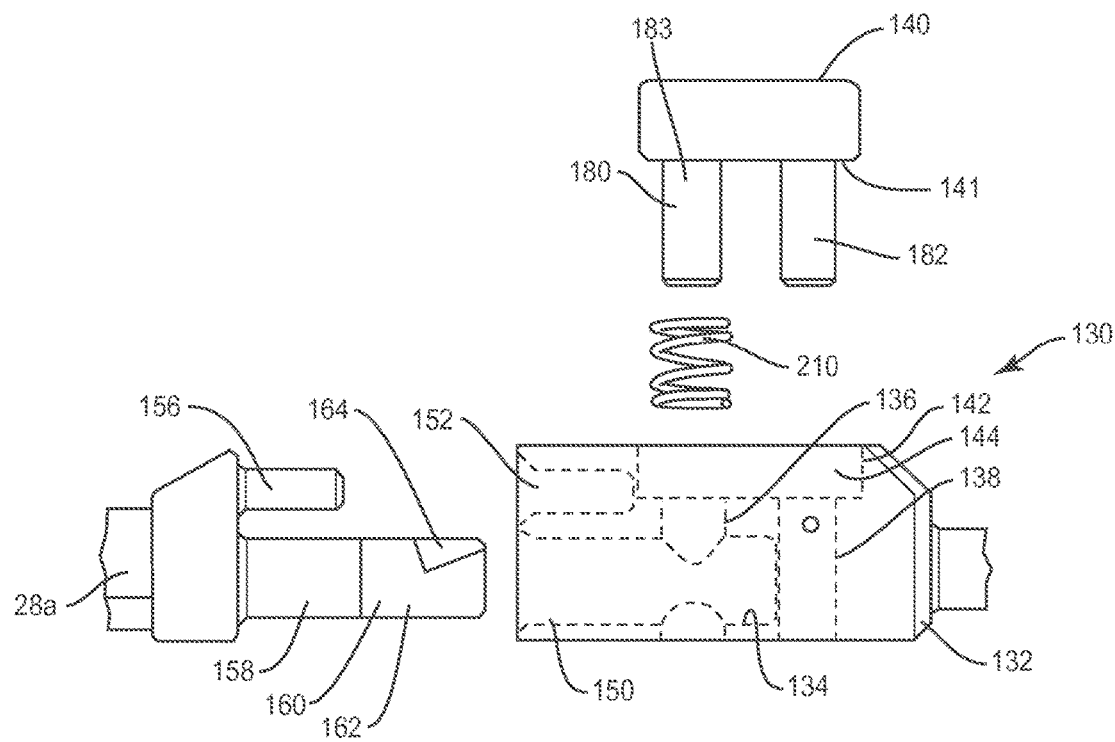
FIG. 3 is a break away side view of components of one embodiment of a surgical system in accordance with the principles of the present disclosure with parts separated.

The exemplary embodiments of the surgical system and related methods of use disclosed are discussed in terms of medical devices for the treatment of musculoskeletal disorders and more particularly, in terms of a surgical system for implant delivery to a surgical site and a method for treating a spine, which employ an oblique surgical pathway. In some embodiments, the surgical systems and methods of the present disclosure are employed with a spinal joint fusion, for example, with a cervical, thoracic, lumbar and/or sacral region of a spine. In some embodiments, the surgical system includes implants and surgical instruments for performing a spinal joint fusion in the L5-S1 disc space from an oblique-lateral surgical pathway at a selected oblique angle from the medial plane of the patient. For example, in some exemplary embodiments, the surgical pathway is established at approximately 15 degrees from a medial plane of a patient while the patient is positioned on their side.

In some embodiments, the surgical system is employed with a method including an oblique lateral interbody fusion (OLIF) procedure in the lower lumbar region between an L5 vertebral body and a sacrum S1 approach using location of a retroperitoneal anatomy and related vascular structures, which may include trans-abdominal and retroperitoneal. In some embodiments, the procedure avoids dissection of the retroperitoneal space and can be done with a small incision using semi-constrained retractors. In some embodiments, the OLIF procedure avoids the psoas muscle, the iliac crest and both branches of the vasculature in the lower lumbar region. Various embodiments may allow for an oblique lower lumbar procedure that is approached between branched vasculature on an anterior side of a patient in a lower lumbar region, for example, at the L5-S1 vertebral levels.

In some embodiments, the surgical system is employed with a method that uses a surgical pathway that is 0-30 degrees off a direct anterior axis of a body. In some embodiments, the surgical pathway is 15 degrees off a direct anterior axis of the body. In some embodiments, the surgical system comprises surgical instruments that include image guided technologies, such as, for example, surgical navigation components employing emitters and sensors, which may be employed to track introduction and/or delivery of the components of the surgical system including the surgical instruments to a surgical site.

In some embodiments, the surgical system comprises a surgical instrument, such as, for example, a surgical retractor employed with an OLIF procedure for accessing the L5-S1 vertebral levels along an antero-lateral corridor. In some embodiments, the surgical system comprises a surgical instrument, such as, for example, a three arm retractor comprising three articulating arms configured for attachment to a fixed straight rail. In some embodiments, the surgical system comprises a surgical instrument, such as, for example, a three arm retractor comprising three articulating arms configured for attachment to a curved rail. In some embodiments, the surgical system comprises a surgical instrument, such as, for example, a three arm retractor comprising three articulating arms configured for attachment to a fixed hub. In some embodiments, the retractor includes blades. In some embodiments, the blades are attached to the three arm retractor. In some embodiments, the surgical system comprises a surgical instrument, such as, for example, a three arm frame retractor configured to position OLIF51 blades.

In some embodiments, the surgical system comprises a surgical instrument, such as, for example, a surgical retractor that comprises three independent arms and three blades. In some embodiments, the surgical retractor is employed with a method that uses an oblique retroperitoneal approach to the L5-S1 space with the patient positioned in a lateral decubitus position. In some embodiments, the surgical retractor comprises three flex arms with one or a plurality of articulation points attached along a straight or curved rail, which may attach directly to a surgical table. In some embodiments, the surgical retractor attaches directly at a hub, which can be attached directly to a surgical table. In some embodiments, the surgical system comprises a blade stabilization pin and a driver.

In some embodiments, the surgical system is employed with a method that is configured for insertion with a lateral anatomy from T12 to S1 vertebral levels along a retroperitoneal corridor that is formed by bony anatomy of ribs, pelvis and the psoas muscle underneath a body. In some embodiments, the surgical system is employed with a method that uses an approach from T12 to L2 vertebral levels, where the approach may be a direct lateral approach to avoid the ribs ventrally. In some embodiments, the method includes the step of retracting and/or dilating the psoas muscle at these levels. In some embodiments, the method includes the step of accessing the L2 to L4 region, which is generally beneath or caudal to the ribs with the psoas transitioning more anteriorly, such that a more oblique anterior approach is employed to avoid violation or minimize retraction. In some embodiments, the method includes the step of moving the trajectory or approach anteriorly to avoid restricted access from the pelvis, which can restrict lateral access in the L4-L5 region, with the psoas transitioning further anterior. In some embodiments, the method includes the step of moving the trajectory or approach anteriorly to avoid restricted access due to bifurcation of vessels laterally to provide safe access to the L5-S1 disc space from a more anterior approach, which can be accomplished at an oblique angle with the patient in the lateral position.

In some embodiments, the surgical system comprises a retractor system that accommodates different anatomic needs when accessing the spine laterally. In some embodiments, the surgical system comprises a plurality of independent fixation arms that each articulate with several degrees of freedom. In some embodiments, each fixation arm comprises a distal end and a proximal end. In some embodiments, the distal end connects to a retractor blade and the proximal end connects to a common rail. In some embodiments, the surgical system comprises a retractor system that comprises a plurality of fixation arms where the plurality of fixation arms each include a distal end and a proximal end, and the distal end connects to a rail comprising a pivot point and a common rail. In some embodiments, the common rail geometry is configured to be contoured to a patient's body or provide localization to a distal fixation tip. In some embodiments, the connection for the proximal end of the fixation arm can be configured to be fixed or modular to make use of multiple attachment points to the common rail.

In some embodiments, the surgical system comprises a retractor system having an alternate proximal attachment and a contoured rail geometry. In some embodiments, the surgical system comprises a retractor system having fixation members that can be located on a central body in a hub configuration. In some embodiments, the fixation members extend from the hub. In some embodiments, fixation members attach to a plurality of retractor blades. In some embodiments, the blades are manipulated into position using a detachable handle. In some embodiments, the position is held once the fixation members are locked. In some embodiments, a locking knob holds a fixation member's orientation. In some embodiments, the plurality of blades combined with degrees of freedom offered by independent fixation arms results in a system that can be used for a variety of embodiments. In some embodiments, each blade achieves a unique angle of trajectory and is unconstrained by placement of adjacent blades.

In some embodiments, the surgical system comprises a retractor system having a connection between at least one fixation arm and at least one retractor blade that provides three degrees of freedom. In some embodiments, the connection includes two degrees of freedom in rotation and one degree of freedom for translation. In some embodiments, the fixation arm comprises a jaw and a collar assembly that is drawn together using a threaded knob. In some embodiments, the assembly comprises a spring and is spring loaded in a dosed position or an up position to provisionally retain a shaft connected with the blade before it is locked. In some embodiments, the assembly can be locked at a selected angle relative to the fixation arm. In some embodiments, the fixation arm comprises a collar component and a jaw component. In some embodiments, the assembly comprises a spring in a selected location and the spring preloads the assembly. In some embodiments, the assembly is preloaded in an upward direction. In some embodiments, the jaw component includes a lead in edge that allows a snap on provisional connection.

In some embodiments, the surgical system comprises OLIF51 access instruments. In some embodiments, the surgical system comprises a thin vessel blade. In some embodiments, the surgical system comprises a wide vessel blade. In some embodiments, the surgical system comprises a blade similar to a Hohmann blade. In some embodiments, the surgical system comprises a stability pin. In some embodiments, the surgical system comprises a pin driver.

In some embodiments, the surgical system comprises a retractor system having a quick connect attachment between at least one fixation arm and at least one retractor blade. In some embodiments, the attachment includes a quick connect device configured to prevent and/or resist toggle between the at least one fixation arm and the at least one retractor blade. In some embodiments, the quick connect device includes a set of ramps under a spring load to drive components together to prevent and/or resist toggle within the connection. In some embodiments, the attachment includes an anti-rotation pin configured to lock a rotational freedom of a joint. In some embodiments, the attachment includes a main pin with a ramp lock geometry. In some embodiments, the attachment includes a quick release button including a ramp lock pin on a side and an anti-rotation pin on another side. In some embodiments, the attachment includes a lead in and locking ramp disposed with components. In some embodiments, the lead in ramp is configured to overcome a force applied by a spring. In some embodiments, a spring pressure is applied to an angle of the locking ramp to retain the components.

In some embodiments, the attachment includes flat components. In some embodiments, the attachment includes tapered components. In some embodiments, the tapered components reduce toggle between the components to substantially zero. In some embodiments, the tapered components include a male component and a female component. In some embodiments, a ramp lock mechanism drives the tapered components into engagement.

In some embodiments, the attachment includes two dowel pins configured to facilitate alignment and isolate rotational loads. In some embodiments, the attachment includes an oval shaped anti-rotation device configured as part of a main pin. In some embodiments, the oval shaped anti-rotation device is machineable to a high degree of accuracy relative to two separate pins.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context dearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, muscle, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIG. 1, there are illustrated components of a surgical system 10.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, bioompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Surgical system 10 may be employed, for example, with minimally invasive procedures, including percutaneous techniques, mini-open surgical techniques and/or open surgical techniques to deliver and introduce instrumentation and/or implants at a surgical site within a subject body B of a patient, which includes, for example, a spine having vertebrae V, as shown in FIGS. 18-30. In some embodiments, surgical system 10 can include spinal constructs, such as, for example, bone fasteners, spinal rods, connectors and/or plates. In other embodiments, various components of surgical system 10 may also be utilized in open or traditional spinal surgical techniques. In many of the embodiments described herein, the patient is positioned on their side for the surgical procedure and the surgeon may stand on an anterior side of the patient to be capable of standing directly above the oblique-anterior and/or oblique lateral surgical pathway established.

Surgical system 10 includes a surgical instrument, such as, for example, a surgical retractor 12, as shown in FIG. 1. Surgical retractor 12 includes an element, such as, for example, a rail 14. Rail 14 is configured for connection with a fixture, such as, for example, an arm 11 of stationary surgical equipment, such as, for example, a surgical table (not shown). Rail 14 is configured to facilitate placement and/or orientation of retractor 12 relative to subject body B and/or an incision in connection with a surgical procedure.

Rail 14 has a cylindrical configuration and extends between an end 16 and an end 18. Rail 14 extends linearly between ends 16, 18. In some embodiments, rail 14 is movable relative to arm 11 and is lockable with arm 11 in a selected position and/or orientation. In some embodiments, rail 14 includes a knob 15 that locks rail 14 with arm 11 in a selected position and/or orientation relative to the surgical table and/or a patient body, as described herein. In some embodiments, knob 15 is connected with a collar 15a having a radially splined surface 15b that engages a radially splined surface 11b of a collar 11a of arm 11 to facilitate incremental and selective positioning of rail 14 relative to the surgical table. Upon selective positioning and orientation of rail 14 relative to arm 11, knob 15 is rotated to force the splined surfaces into engagement for locking rail 14 in position with arm 11.

In some embodiments, rail 14 can include a single or multiple rails, each being spaced apart from one another and disposed in various orientations, such as, for example, offset, staggered, transverse, perpendicular and/or parallel. In some embodiments, all or only a portion of rail 14 may be variously configured and dimensioned, such as, for example, planar, concave, convex, polygonal, irregular, uniform, non-uniform, staggered, tapered, consistent or variable.

Surgical retractor 12 includes a plurality of members, such as, for example, a plurality of retractor arms 20, 60 and 90, as described herein. Retractor arms 20, 60, 90 are attached with rail 14 such that one or a plurality of arms 20, 60, 90 are movable in one or a plurality of degrees of freedom to one or a plurality of orientations relative to rail 14, stationary surgical equipment and/or subject body B in connection with a surgical procedure. In some embodiments, the degrees of freedom of movement of one or more of arms 20, 60, 90 to one or a plurality of orientations relative to rail 14, stationary surgical equipment and/or subject body B can include one or a plurality of degrees of movement in translation, one or a plurality of degrees of movement in rotation, planar movement such as a four bar linkage, spherical movement such as poly-axial and/or joints or links such as a kinematic chain. In some embodiments, the degrees of movement in translation can include up, down, left, right, forward and/or backward. In some embodiments, the degrees of movement in rotation can include tilting, swiveling and/or pivoting in one or a plurality directions.

In some embodiments, arms 20, 60, 90 are independently and selectively movable relative to rail 14, stationary surgical equipment and/or subject body B. In some embodiments, arms 20, 60, 90 comprise a plurality of independent fixation arms that each articulate with several degrees of freedom relative to rail 14, stationary surgical equipment and/or subject body B. In some embodiments, the configuration of surgical retractor 12 provides arms 20, 60, 90 that can be employed with a variety of surgical applications, as described herein. In some embodiments, the configuration of surgical retractor 12 provides arms 20, 60, 90 connected to parts, such as, for example, blades that can be disposed at a selected angle of trajectory and unconstrained by placement of adjacent blades. In some embodiments, arms 20, 60, 90 are attached with rail 14 in a modular configuration to facilitate attachment at multiple attachment points, as described herein.

Arm 20 is connected with rail 14 at a projection 17a adjacent an end portion of rail 14. Projection 17a defines an axis X1. Projection 17a includes a bearing, such as, for example, a ball 26 that is connected with arm 20, as described herein. Arm 20 is movable in a plurality of degrees of freedom to one or a plurality of orientations, relative to rail 14, stationary surgical equipment and/or subject body B in connection with a surgical procedure. In some embodiments, arm 20 is independently and selectively moveable relative to rail 14 about axis X1 to facilitate positioning of a part, such as, for example, a blade 28 (FIG. 18), as described herein.

Arm 20 includes an extension 22 and an extension 24. Extension 22 includes a tubular collar 32 that defines a socket 34 configured for disposal of ball 26. Ball 26 and collar 32 form a spheroidal joint, such as, for example, a ball joint 30 that facilitates relative movement of extension 22 and rail 14. Ball 26 is fixed with rail 14 and collar 32 is movable thereabout such that extension 22 is movable in a plurality of degrees of freedom to one or a plurality of orientations, such as, for example, poly-axial relative to rail 14, stationary surgical equipment and/or subject body B in connection with a surgical procedure. In some embodiments, ball joint 30 provides rotation of extension 22 relative to projection 17a and disposal of extension 22 at a plurality of orientations relative to axis X1. In some embodiments, extension 22 is movable relative to rail 14 between a first orientation and a second orientation in which extension 22 is moveable through an angular range relative to axis X1. In some embodiments, the orientations relative to axis X1 may include, such as, for example, transverse, perpendicular, angular orientations such as acute or obtuse, coaxial and/or may be offset or staggered.

Extension 22 includes a disc shaped collar 36 that is connected to a disc shaped collar 40 of extension 24, as described herein. Collars 36, 40 form a pivot joint 37 that is disposable between a movable orientation and a locked orientation. Pivot joint 37 defines an axis A1 disposed transverse to axis X1. Collars 36, 40 are relatively rotatable about axis A1 to facilitate rotation of extension 24 relative to extension 22 for positioning of blade 28 relative to rail 14, stationary surgical equipment and/or subject body B.

Pivot joint 37 includes a knob 38 that locks collar 36 with collar 40 such that extensions 22, 24 are disposed in a selected relative position and/or orientation relative to rail 14, stationary surgical equipment and/or subject body B. In some embodiments, knob 38 is connected with collar 36 having a radially splined surface that engages a radially splined surface of collar 40 to facilitate incremental and selective positioning of extensions 22, 24. Upon selective positioning and orientation of extensions 22, 24, knob 38 is rotated to force the splined surfaces into engagement for locking extension 22 in position with extension 24.

Extension 24 includes a tubular collar 42 that defines a socket 43. Socket 43 is configured for disposal of a bearing, such as, for example, a ball 44. Ball 44 and collar 42 form a spheroidal joint, such as, for example, a ball joint 46 that facilitates relative movement of blade 28 and extension 24. Blade 28 is movable in a plurality of degrees of freedom to one or a plurality of orientations, relative to extension 24, stationary surgical equipment and/or subject body B in connection with a surgical procedure. In some embodiments, blade 28 is independently and selectively moveable relative to extension 24 about axis X1 to facilitate positioning of blade 28, as described herein.

Extension 24 includes a damp 50 for connection with blade 28. Clamp 50 is adjustable for releasable engagement with blade 28 to fix blade 28 in a selected orientation with arm 20. Clamp 50 includes a projection 51 that includes ball 44 for engagement with socket 43, as described herein, to facilitate relative movement of blade 28 and extension 24 in a plurality of degrees of freedom, such as poly-axial to one or a plurality of orientations. In some embodiments, damp 50 includes a surface 52 that defines a cavity 54 configured for disposal of an arm 28a (FIG. 18) of blade 28, as described herein. Clamp 50 includes a jaw 56 configured for translation within cavity 54 by actuation of a handle 58. Handle 58 is rotated such that jaw 56 engages arm 28a to fix blade 28 with damp 50.

Figure 18:
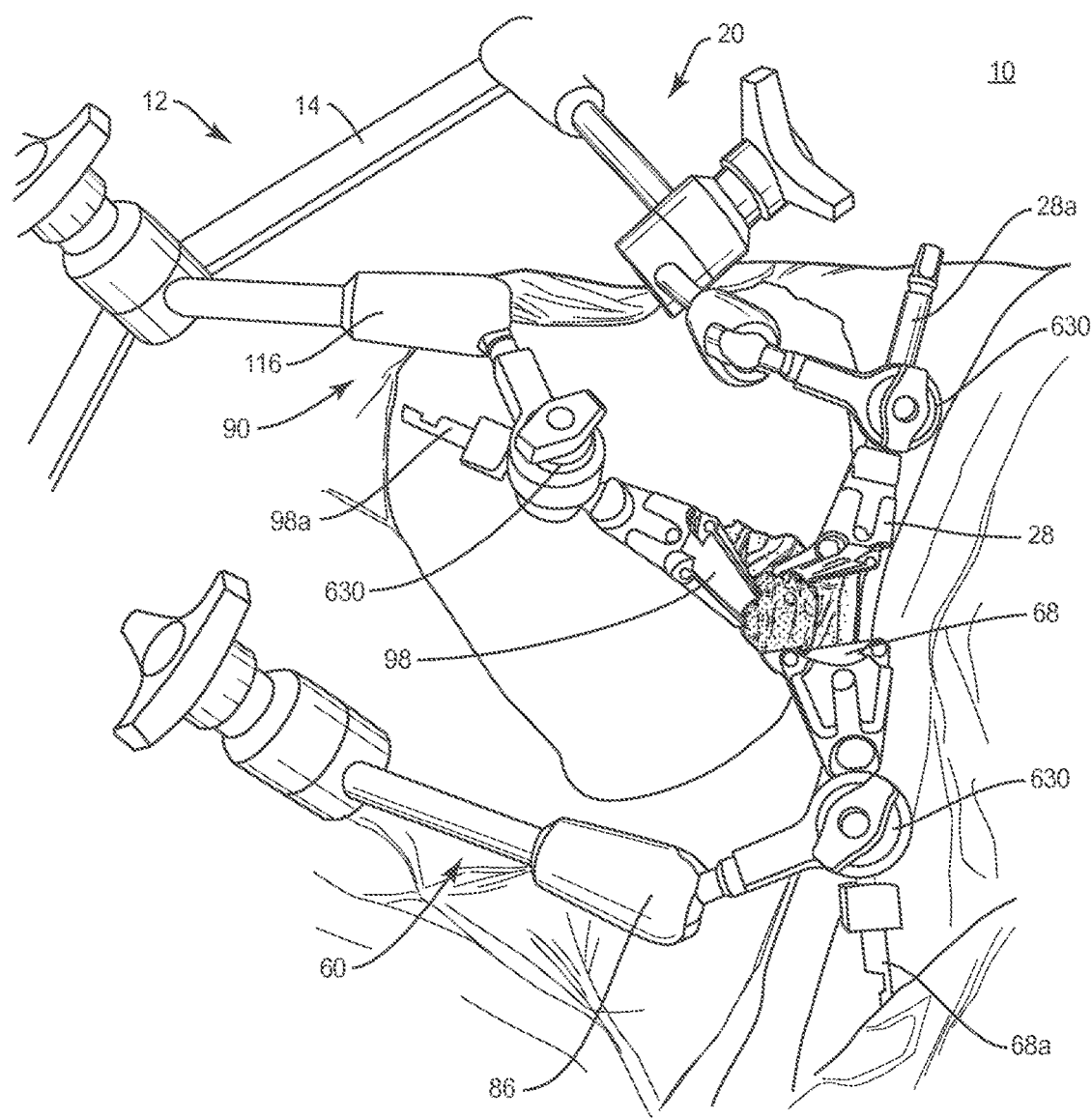
FIG. 18 is a plan view of components of one embodiment of a surgical system in accordance with the principles of the present disclosure disposed with a subject body.

In some embodiments, blade 28 is configured for disposal in a posterior orientation and engageable with tissue of a substantially posterior portion of an incision relative to subject body B, as described herein. In some embodiments, blade 28 is disposable in a configuration to space tissue of the incision to define an oblique surgical pathway P relative to a bilateral axis of subject body B, as described herein. In some embodiments, blade 28 is movable relative to extension 24 between a first orientation and a second orientation in which blade 28 is moveable through an angular range relative to extension 24 via ball joint 46. In some embodiments, blade 28 is configured to achieve a unique angle of trajectory and is unconstrained by placement of adjacent blades, as described herein. In some embodiments, blade 28 extends between a first end and a second end. Blade 28 includes an outer surface configured for engaging and spacing apart tissue. Blade 28 includes an inner surface configure to define a portion of surgical pathway P. Blade 28 includes arm 28a, as shown in FIG. 18, configured for engagement with arm 20, as described herein, or with an adaptor, as described herein.

Arm 60 is connected with rail 14 at a projection 17b adjacent an intermediate portion of rail 14. Projection 17b defines an axis X2. Projection 17b includes a bearing, such as, for example, a ball 66 that is connected with arm 60, as described herein. Arm 60 is movable in a plurality of degrees of freedom to one or a plurality of orientations, relative to rail 14, stationary surgical equipment and/or subject body B in connection with a surgical procedure. In some embodiments, arm 60 is independently and selectively moveable relative to rail 14 about axis X2 to facilitate positioning of a part, such as, for example, a blade 68 (FIG. 18), as described herein.

Arm 60 includes an extension 62 and an extension 64. Extension 62 includes a tubular collar 72 that defines a socket 69 configured for disposal of ball 66. Ball 66 and collar 72 form a spheroidal joint, such as, for example, a ball joint 70 that facilitates relative movement of extension 62 and rail 14. Ball 66 is fixed with rail 14 and collar 72 is movable thereabout such that extension 62 is movable in a plurality of degrees of freedom to one or a plurality of orientations, such as, for example, poly-axial relative to rail 14, stationary surgical equipment and/or subject body B in connection with a surgical procedure. In some embodiments, ball joint 70 provides rotation of extension 62 relative to projection 17b and disposal of extension 62 at a plurality of orientations relative to axis X2. In some embodiments, extension 62 is movable relative to rail 14 between a first orientation and a second orientation in which extension 62 is moveable through an angular range relative to axis X2. In some embodiments, the orientations relative to axis X2 may include, such as, for example, transverse, perpendicular, angular orientations such as acute or obtuse, coaxial and/or may be offset or staggered.

Extension 62 includes a disc shaped collar 76 that is connected to a disc shaped collar 80 of extension 64, as described herein. Collars 76, 80 form a pivot joint 77 that is disposable between a movable orientation and a locked orientation. Pivot joint 77 defines an axis A2 disposed transverse to axis X2. Collars 76, 80 are relatively rotatable about axis A2 to facilitate rotation of extension 64 relative to extension 62 for positioning of blade 68 relative to rail 14, stationary surgical equipment and/or subject body B.

Pivot joint 77 includes a knob 78 that locks collar 76 with collar 80 such that extensions 62, 64 are disposed in a selected relative position and/or orientation relative to rail 14, stationary surgical equipment and/or subject body B. In some embodiments, knob 78 is connected with collar 76 having a radially splined surface that engages a radially splined surface of collar 80 to facilitate incremental and selective positioning of extensions 62, 64. Upon selective positioning and orientation of extensions 62, 64, knob 78 is rotated to force the splined surfaces into engagement for locking extension 62 in position with extension 64.

Extension 64 includes a tubular collar 82 that defines a socket 83. Socket 83 is configured for disposal of a bearing, such as, for example, a ball 84. Ball 84 and collar 82 form a spheroidal joint, such as, for example, a ball joint 86 that facilitates relative movement of blade 68 and extension 64. Blade 68 is movable in a plurality of degrees of freedom to one or a plurality of orientations, relative to extension 64, stationary surgical equipment and/or subject body B in connection with a surgical procedure. In some embodiments, blade 68 is independently and selectively moveable relative to extension 64 about axis X2 to facilitate positioning of blade 68, as described herein.

Extension 64 includes a damp 88 for connection with blade 68. Clamp 88 is adjustable for releasable engagement with blade 68 to fix blade 68 in a selected orientation with arm 60. Clamp 88 includes a projection 89 that includes ball 84 for engagement with socket 83, as described herein, to facilitate relative movement of blade 68 and extension 64 in a plurality of degrees of freedom, such as poly-axial to one or a plurality of orientations. In some embodiments, damp 88 includes a surface 88a that defines a cavity 88b configured for disposal of an arm 68a (FIG. 18) of blade 68, as described herein. Clamp 88 includes a jaw 88c configured for translation within cavity 88b by actuation of a handle 88d. Handle 88d is rotated such that jaw 88c engages arm 68a to fix blade 68 with damp 88.

In some embodiments, blade 68 is configured for disposal in an anterior orientation and engageable with tissue of a substantially anterior portion of an incision relative to subject body B, as described herein. In some embodiments, blade 68 is disposable in a configuration to space tissue of the incision to define an oblique surgical pathway P relative to a bilateral axis of subject body B, as described herein. In some embodiments, blade 68 is movable relative to extension 64 between a first orientation and a second orientation in which blade 68 is moveable through an angular range relative to extension 64 via ball joint 86. In some embodiments, blade 68 is configured to achieve a unique angle of trajectory and is unconstrained by placement of adjacent blades, as described herein. In one embodiment, blade 68 extends between a first end and a second end. Blade 68 includes an outer surface configured for engaging and spacing apart tissue. Blade 68 includes an inner surface configure to define a portion of surgical pathway P. Blade 68 includes arm 68a, as shown in FIG. 18, configured for engagement with arm 60 and or an adaptor, as described herein.

Arm 90 is connected with rail 14 at a projection 17c adjacent an end portion of rail 14. Projection 17c defines an axis X3. Projection 17c includes a bearing, such as, for example, a ball 96 that is connected with arm 90, as described herein. Arm 90 is movable in a plurality of degrees of freedom to one or a plurality of orientations, relative to rail 14, stationary surgical equipment and/or subject body B in connection with a surgical procedure. In some embodiments, arm 90 is independently and selectively moveable relative to rail 14 about axis X3 to facilitate positioning of a part, such as, for example, a blade 98 (FIG. 18), as described herein.

Arm 90 includes an extension 92 and an extension 94. Extension 92 includes a tubular collar 102 that defines a socket 104 configured for disposal of ball 96. Ball 96 and collar 102 form a spheroidal joint, such as, for example, a ball joint 100 that facilitates relative movement of extension 92 and rail 14. Ball 96 is fixed with rail 14 and collar 102 is movable thereabout such that extension 92 is movable in a plurality of degrees of freedom to one or a plurality of orientations, such as, for example, poly-axial relative to rail 14, stationary surgical equipment and/or subject body B in connection with a surgical procedure. In some embodiments, ball joint 100 provides rotation of extension 92 relative to projection 17c and disposal of extension 92 at a plurality of orientations relative to axis X3. In some embodiments, extension 92 is movable relative to rail 14 between a first orientation and a second orientation in which extension 92 is moveable through an angular range relative to axis X3. In some embodiments, the orientations relative to axis X3 may include, such as, for example, transverse, perpendicular, angular orientations such as acute or obtuse, coaxial and/or may be offset or staggered.

Extension 92 includes a disc shaped collar 106 that is connected to a disc shaped collar 110 of extension 94, as described herein. Collars 106, 110 form a pivot joint 107 that is disposable between a movable orientation and a locked orientation. Pivot joint 107 defines an axis A3 disposed transverse to axis X3. Collars 106, 110 are relatively rotatable about axis A3 to facilitate rotation of extension 94 relative to extension 92 for positioning of blade 98 relative to rail 14, stationary surgical equipment and/or subject body B.

Pivot joint 107 includes a knob 108 that locks collar 106 with collar 110 such that extensions 92, 94 are disposed in a selected relative position and/or orientation relative to rail 14, stationary surgical equipment and/or subject body B. In some embodiments, knob 108 is connected with collar 106 having a radially splined surface that engages a radially splined surface of collar 110 to facilitate incremental and selective positioning of extensions 92, 94. Upon selective positioning and orientation of extensions 92, 94, knob 108 is rotated to force the splined surfaces into engagement for locking extension 92 in position with extension 94.

Extension 94 includes a tubular collar 112 that defines a socket 113. Socket 113 is configured for disposal of a bearing, such as, for example, a ball 114. Ball 114 and collar 112 form a spheroidal joint, such as, for example, a ball joint 116 that facilitates relative movement of blade 98 and extension 94. Blade 98 is movable in a plurality of degrees of freedom to one or a plurality of orientations, relative to extension 94, stationary surgical equipment and/or subject body B in connection with a surgical procedure. In some embodiments, blade 98 is independently and selectively moveable relative to extension 94 about axis X1 to facilitate positioning of blade 98, as described herein.

Extension 94 includes a damp 118 for connection with blade 98. Clamp 118 is adjustable for releasable engagement with blade 98 to fix blade 98 in a selected orientation with arm 90. Clamp 118 includes a projection 119 that includes ball 114 for engagement with socket 113, as described herein, to facilitate relative movement of blade 98 and extension 94 in a plurality of degrees of freedom, such as poly-axial to one or a plurality of orientations. In some embodiments, clamp 118 includes a surface 118a that defines a cavity 118b configured for disposal of an arm 98a (FIG. 18) of blade 98, as described herein. Clamp 118 includes a jaw 118c configured for translation within cavity 118b by actuation of a handle 118d. Handle 118d is rotated such that jaw 118c engages arm 98a to fix blade 98 with clamp 118.

In some embodiments, blade 98 is configured for disposal in a cephalad orientation and engageable with tissue of a substantially cephalad portion of an incision relative to subject body B, as described herein. In some embodiments, blade 98 is disposable in a configuration to space tissue of the incision to define an oblique surgical pathway P relative to a bilateral axis of subject body B, as described herein. In some embodiments, blade 98 is movable relative to extension 94 between a first orientation and a second orientation in which blade 98 is moveable through an angular range relative to extension 94 via ball joint 116. In some embodiments, blade 98 is configured to achieve a unique angle of trajectory and is unconstrained by placement of adjacent blades, as described herein. In one embodiment, blade 98 extends between a first end and a second end. Blade 98 includes an outer surface configured for engaging and spacing apart tissue. Blade 98 includes an inner surface configure to define a portion of surgical pathway P. Blade 98 includes an arm 98a, as shown in FIG. 18 configured for engagement with arm 90 and or an adaptor, as described herein.

In some embodiments, one or more of the blades connected with arm 20, arm 60 and/or arm 90 can include a thin vessel blade 128a, as shown in FIG. 2a. In some embodiments, one or more of the blades connected with arm 20, arm 60 and/or arm 90 can include a wide vessel blade 128b, as shown in FIG. 2b. In some embodiments, one or more of the blades connected with arm 20, arm 60 and/or arm 90 can include a blade similar to a Hohmann blade 128c, as shown in FIG. 2c. In some embodiments, surgical system 10 can include a stability pin 128d attached with one or more of the blades described herein to fix a blade with tissue, which may be engaged with a pin driver 128e, as shown in FIG. 2e.

In one embodiment, as shown in FIGS. 3-8, surgical system 10 includes an adaptor 130 configured for attaching a member, such as, for example, arm 20 described herein, with a part, such as, for example, blade 28. In some embodiments, adaptor 130 is configured as a quick connect attachment between arm 20 and blade 28, and resists and/or prevents toggle therebetween. In some embodiments, adaptor 130 can be employed with one or more of arms 20, 60, 90 and blades 28, 68, 98, as described herein. In some embodiments, adaptor 130 includes a portion of an arm of a blade, such as, for example, arm 28a and a portion of a member, such as, for example, extension 24. In some embodiments, adaptor 130 is connected with extension 24 and such connection comprises a spheroidal joint, similar to ball joint 46. In some embodiments, adaptor 130 comprises a separate component of surgical system 10 that is attached with arm 20 and blade 28.

Adaptor 130 includes a housing 132. Housing 132 is configured for a mating engagement with extension 24 of arm 20, as described herein. Housing 132 includes a surface 134 that defines a cavity 136 and a cavity 138 configured for disposal of an actuator, such as, for example, a push button 140. Cavities 136, 138 are disposed adjacent in spaced apart relation. In some embodiments, cavities 136, 138 are disposed in parallel. In some embodiments, cavities 136, 138 are disposed in various relative orientations, such as, for example, offset, staggered, transverse, perpendicular and/or angular such as obtuse or acute. Housing 132 includes a surface 142 that defines a recess 144. Recess 144 is configured for disposal of a portion of button 140 in a nested configuration in a selected position, such as, for example, an open and/or release position, as described herein.

Figure 4:
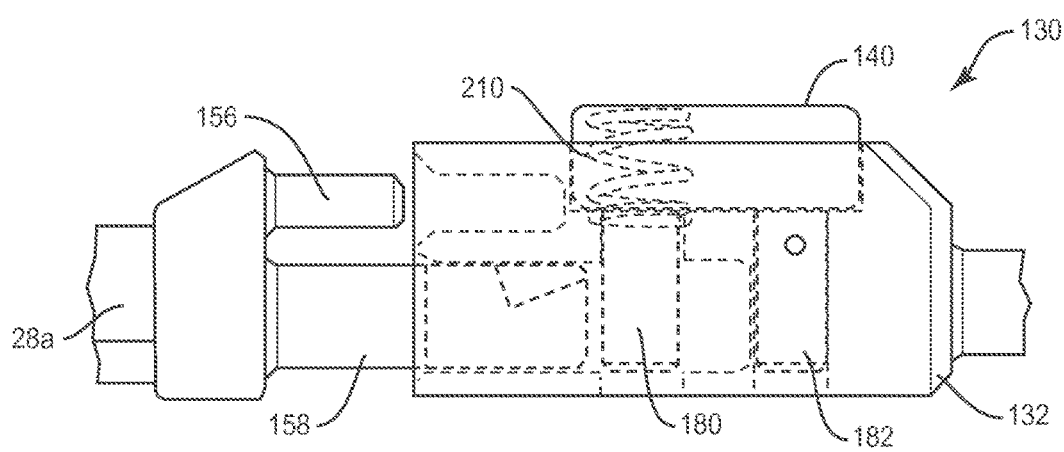
FIG. 4 is a break away side view in cutaway of components of one embodiment of a surgical system in accordance with the principles of the present disclosure.
Figure 5:
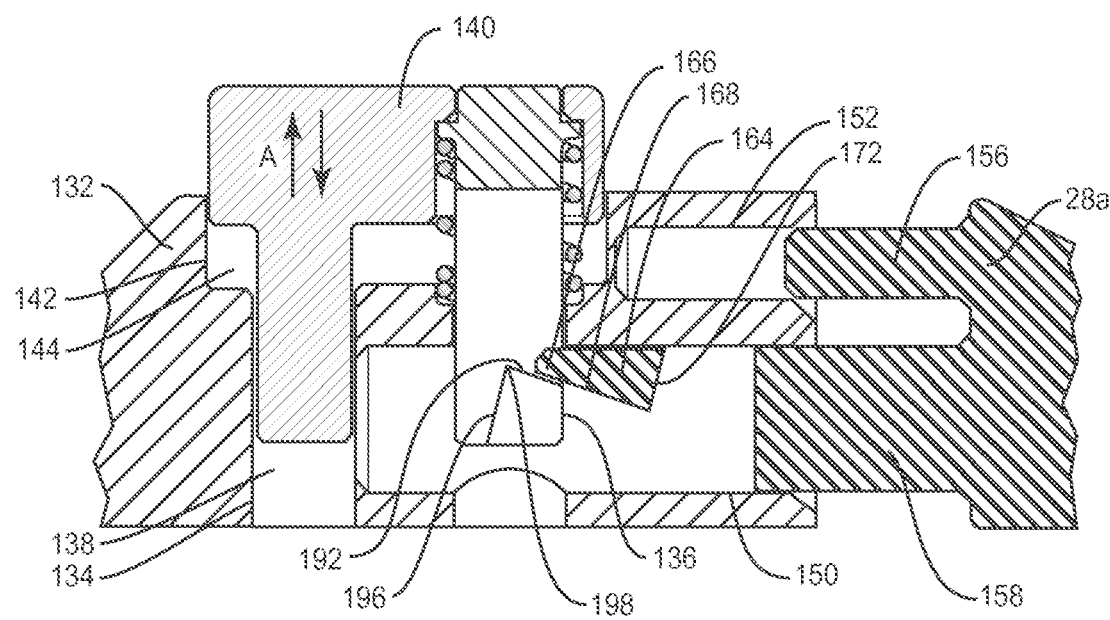
FIG. 5 is a cross section view of the components shown in FIG. 4.
Figure 6:
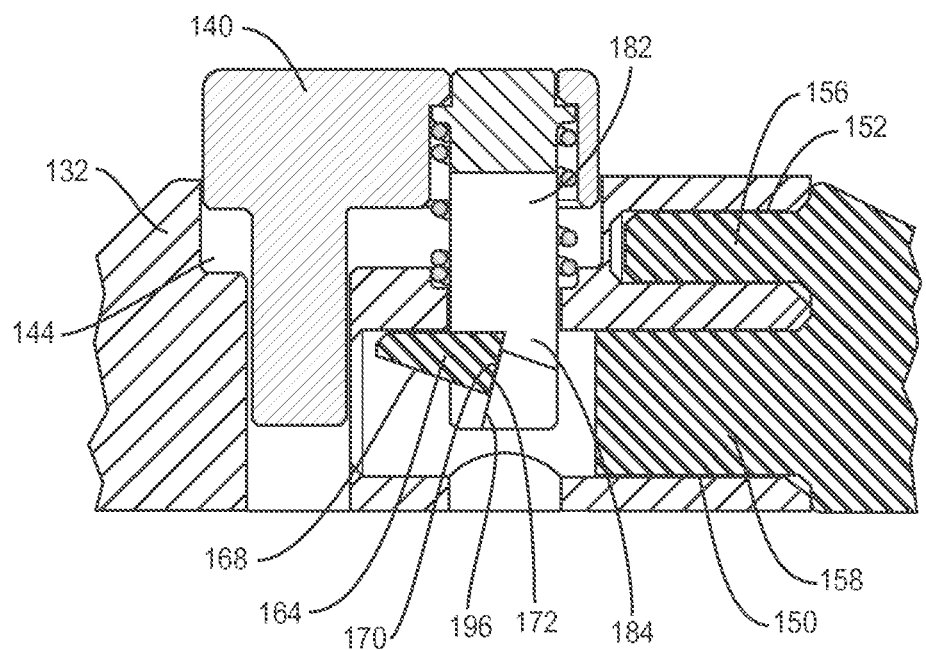
FIG. 6 is a cross section view of the components shown in FIG. 4.
Figure 7:
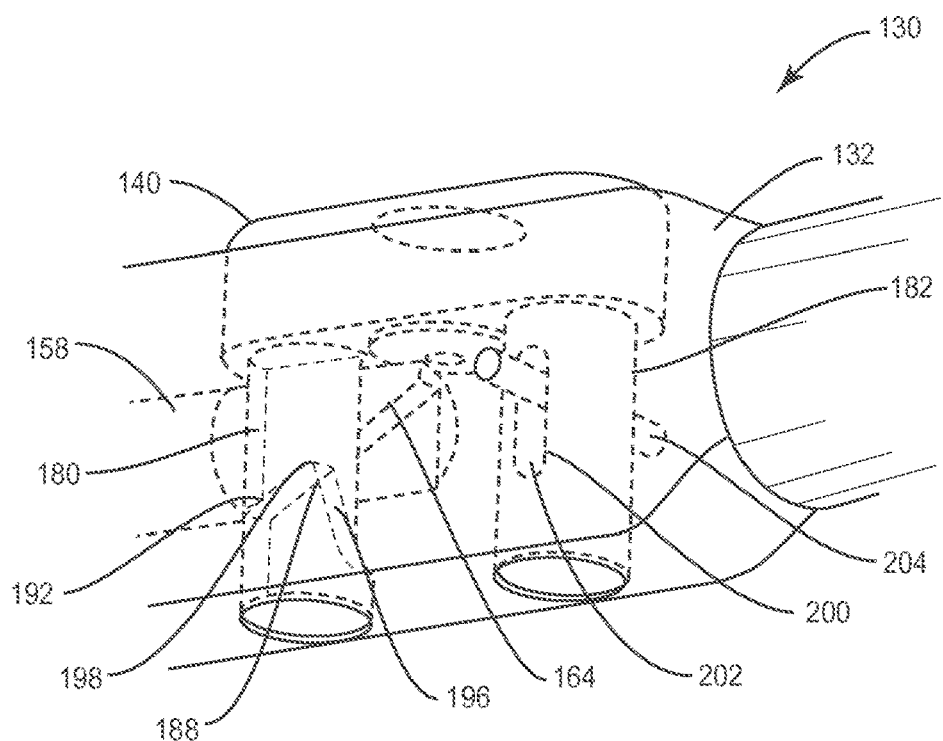
FIG. 7 is a cutaway view of the components shown in FIG. 4.
Figure 8:
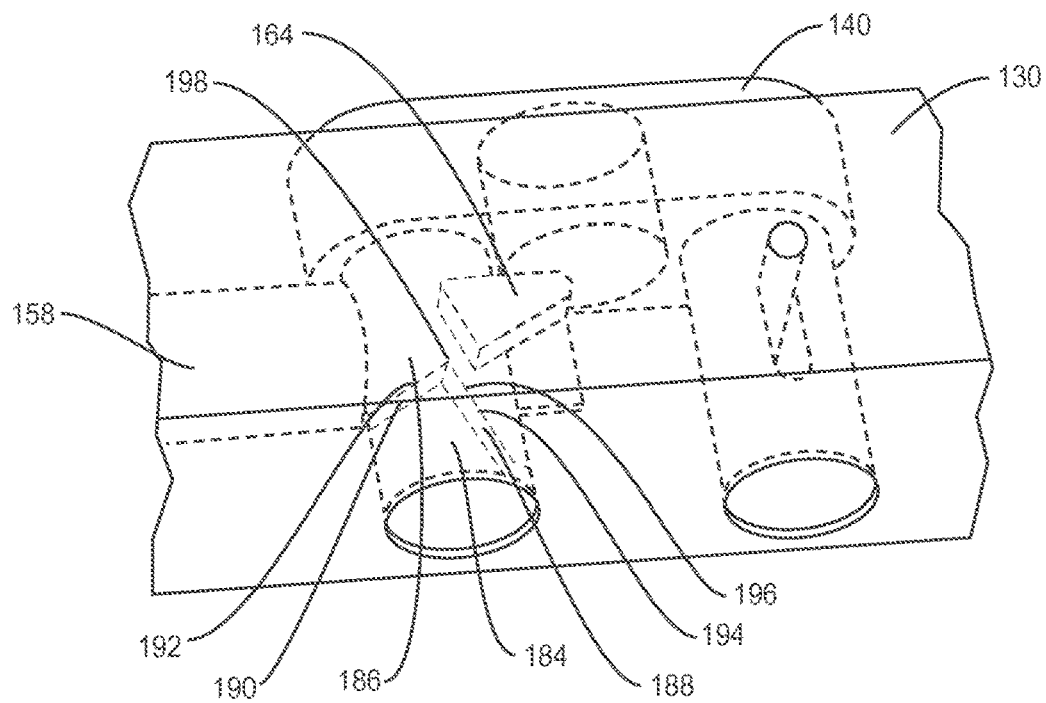
FIG. 8 is a cutaway view of the components shown in FIG. 4.

Surface 134 defines a cavity 150. Cavity 150 is disposed transverse relative to cavities 136, 138. Cavity 150 is in communication with cavity 136 to facilitate translation of arm 28a within and relative to adaptor 130 to dispose blade 28 with arm 20 between a non-locked position, as shown in FIG. 4, and a locked position, as shown in FIG. 6. Button 140 is manipulable via engagement with arm 28a and/or depressible by a practitioner for translation, in the direction shown by arrows A in FIG. 5, to dispose blade 28 with arm 20 between the non-locked position and the locked position. Surface 134 defines a cavity 152 disposed transverse relative to cavities 136, 138. Cavity 152 is configured to receive an anti-rotation element, such as, for example, a pin 156, connected with arm 28a of blade 28, as described herein.

A portion of arm 28a includes a cylinder 158 for disposal within cavity 150. Arm 28a includes a surface 160 that defines a channel 162. Surface 160 includes a wedge 164 disposed with channel 162. Wedge 164 includes a surface 166 that defines a lead ramp 168. Wedge 164 includes a surface 170 that defines a locking ramp 172. Ramps 168, 172 are configured for engagement with a wedge 188, as described herein, to facilitate translation and/or locking of blade 28 with arm 20, as described herein. Disposal of pin 156 with cavity 152 and engagement with surface 134 to resist and/or prevent rotation of arm 28a relative to extension 24.

Button 140 includes a surface 141. An extension 180 and an extension 182 extend from surface 141 into housing 132. Extension 180 is configured for disposal within cavity 136. Extension 180 includes a cylindrical portion 183. Extension 180 includes a surface 184 that defines a channel 186. Surface 184 includes a wedge 188 disposed with channel 186 and configured for engagement with wedge 164, as described herein. Wedge 188 includes a surface 190 that defines a ramp 192. Wedge 188 includes a surface 194 that defines a ramp 196. Ramps 192, 196 form an apex 198. Ramp 168 is configured for slidable engagement with ramp 192 over apex 198 to engage ramp 196 to move button 140 between a locked position and an open position, as described herein. Ramp 172 is configured for slidable engagement with ramp 196 such that adaptor 130 releasably locks blade 28 with arm 20. As ramp 172 translates along ramp 196, wedge 164 translates for disposal in a position such that wedge slides over wedge 188 and is engaged therewith in an interference fit. Spring 210, as described herein, is resiliently biased to maintain wedges 164, 188 in interference and locked orientation to resist and/or prevent arm 28a from disengaging from adaptor 130. In some embodiments, spring 210 is disposed in cavity 136 and configured to apply a force to surface 141 and wedge 164 such that arm 28a is engageable with adaptor 130 and/or button 140 is manipulable, as described herein, such that adaptor 130 is a quick release mechanism.

Extension 182 includes a surface 200 that defines a cavity 202. Cavity 202 is configured for disposal of a pin, such as, for example, an alignment pin 204 configured to facilitate alignment of button 140 with housing 132.

In use, adaptor 130 is disposed in a locked position, as shown in FIG. 4, such that button 140 is nested in recess 144 and spring 210 biases button 140 in the locked position. Cylinder 158 is aligned with cavity 150 and pin 156 is aligned with cavity 152. Pin 156 and cylinder 158 are translated for disposal in cavities 150, 152 and engagement with surface for connection of arm 28*a* with extension 24. Wedge 164 translates through channel 186 and engages wedge 188 such that button 140 translates and the bias force of spring 210 is overcome, as shown in FIG. 5. Translation of wedge 164 through channel 186 causes ramp 168 to translate along ramp 192 to apex 198. Ramp 168 slides over apex 198 to engage ramp 196. Wedge 164 is disposed in a position such that wedge 164 slides over wedge 188 and is engaged therewith in an interference fit. Spring 210 expands to the resiliently biased orientation to maintain wedges 164, 188 in interference and locked orientation to resist and/or prevent arm 28*a* from disengaging from adaptor 130, as shown in FIG. 6. In some embodiments, adaptor 130 is configured as a quick connect attachment between arm 20 and blade 28, and resists and/or prevents toggle therebetween.

Figure 9:
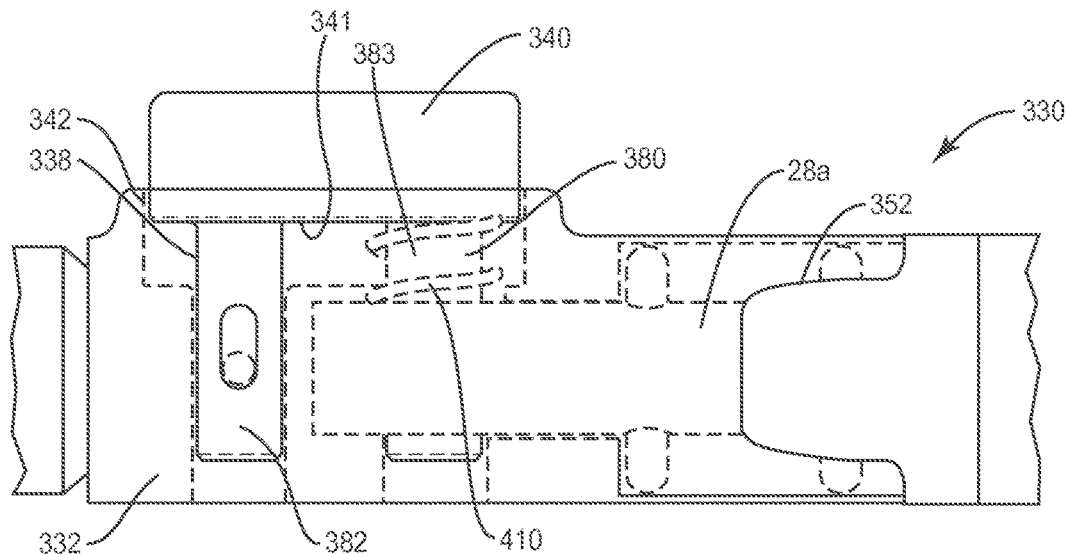
FIG. 9 is a break away side view in cutaway of components of one embodiment of a surgical system in accordance with the principles of the present disclosure.
Figure 10:
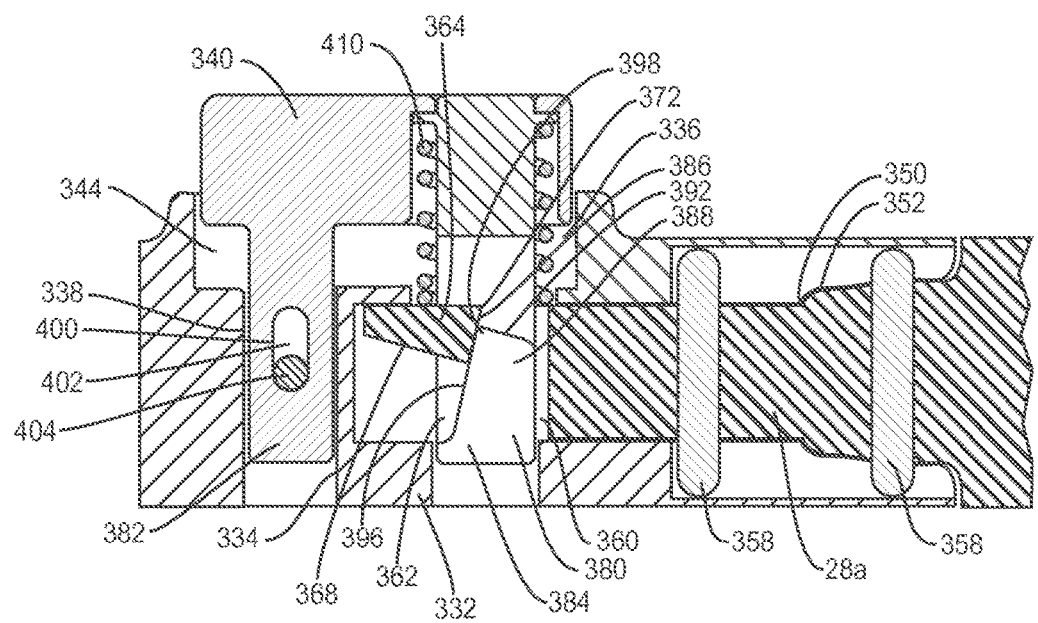
FIG. 10 is a cross section view of the components shown in FIG. 9.

In one embodiment, as shown in FIGS. 9 and 10, surgical system 10, similar to the systems and methods described herein, includes an adaptor 330, similar to adaptor 130 described herein, for attaching a member, such as, for example, arm 20 described herein, with a part, such as, for example, blade 28.

Adaptor 330 includes a housing 332. Housing 332 is configured for a mating engagement with extension 24 of arm 20, as described herein. Housing 332 includes a surface 334 that defines a cavity 336 and a cavity 338 configured for disposal of a push button 340, similar to button 140 described herein. Cavities 336, 338 are disposed adjacent in spaced apart relation. Housing 332 includes a surface 342 that defines a recess 344. Recess 344 is configured for disposal of a portion of button 340 in a nested configuration in a selected position, such as, for example, an open and/or release position, as described herein.

Housing 332 includes a cavity 350 disposed transverse to cavities 336, 338. Cavity 350 is in communication with cavity 336 to facilitate translation of arm 28*a* within and relative to adaptor 330 to dispose blade 28 with arm 20 between a non-locked position and a locked position. Cavity 350 includes a tapered surface 352. Tapered surface 352 is configured to form a friction fit with a surface of arm 28*a*, as described herein. Arm 28*a* includes a tapered configuration and is configured for disposal within cavity 350 in a friction fit configuration. The friction fit of arm 28*a* and surface 352 resists and/or prevents rotation of arm 28*a* relative to extension 24. In some embodiments, arm 28*a* is configured for engagement with dowel pins 358 that are configured to facilitate alignment and isolate rotational loads.

Button 440 is manipulable via engagement with arm 28*a* and/or depressible by a practitioner for translation to dispose blade 28 with arm 20 between the non-locked position and the locked position. Arm 28*a* includes a surface 360 that defines a channel 362. Surface 360 includes a wedge 364 disposed with channel 362. Wedge 364 includes a lead ramp 368. Wedge 364 includes a locking ramp 372. Ramps 368, 372 are configured for engagement with a wedge 388, as described herein, to facilitate translation and/or locking of blade 28 with arm 20, as described herein.

Button 340 includes a surface 341. An extension 380 and an extension 382 extend from surface 341 into housing 332. Extension 380 is configured for disposal within cavity 336. Extension 380 includes a cylindrical portion 383. Extension 380 includes a surface 384 that defines a channel 386. Surface 384 includes a wedge 388 disposed with channel 386 and configured for engagement with wedge 364, as described herein. Wedge 388 defines a ramp 392. Wedge 388 defines a ramp 396. Ramps 392, 396 form an apex 398.

Ramp 368 is configured for slidable engagement with ramp 392 over apex 398 to engage ramp 396 to move button 340 between a locked position and an open position, as described herein. Ramp 372 is configured for slidable engagement with ramp 396 such that adaptor 330 releasably locks blade 28 with arm 20. As ramp 372 translates along ramp 396, wedge 364 translates for disposal in a position such that wedge slides over wedge 388 and is engaged therewith in an interference fit. Spring 410, as described herein, is resiliently biased to maintain wedges 364, 388 in interference and locked orientation to resist and/or prevent arm 28*a* from disengaging from adaptor 330. In some embodiments, spring 410 is disposed in cavity 336 and configured to apply a force to surface 341 and wedge 364 such that arm 28*a* is engageable with adaptor 330 and/or button 340 is manipulable, as described herein, such that adaptor 330 is a quick release mechanism.

Extension 382 includes a surface 400 that defines a cavity 402. Cavity 402 is configured for disposal of a pin, such as, for example, an alignment pin 404 configured to facilitate alignment of button 340 with housing 332.

Figure 11:
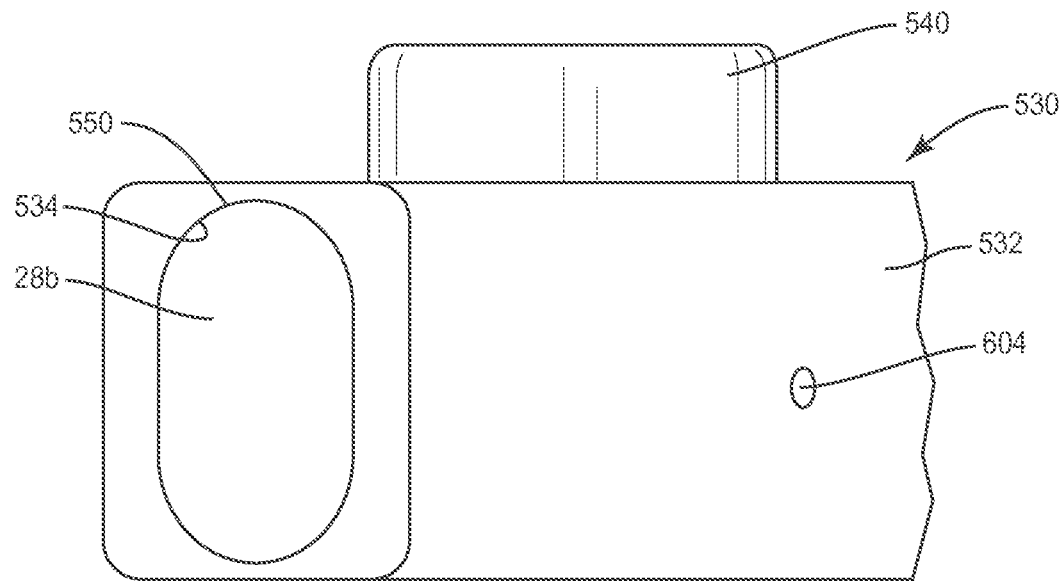
FIG. 11 is a break away perspective view of components of one embodiment of a surgical system in accordance with the principles of the present disclosure.
Figure 12:
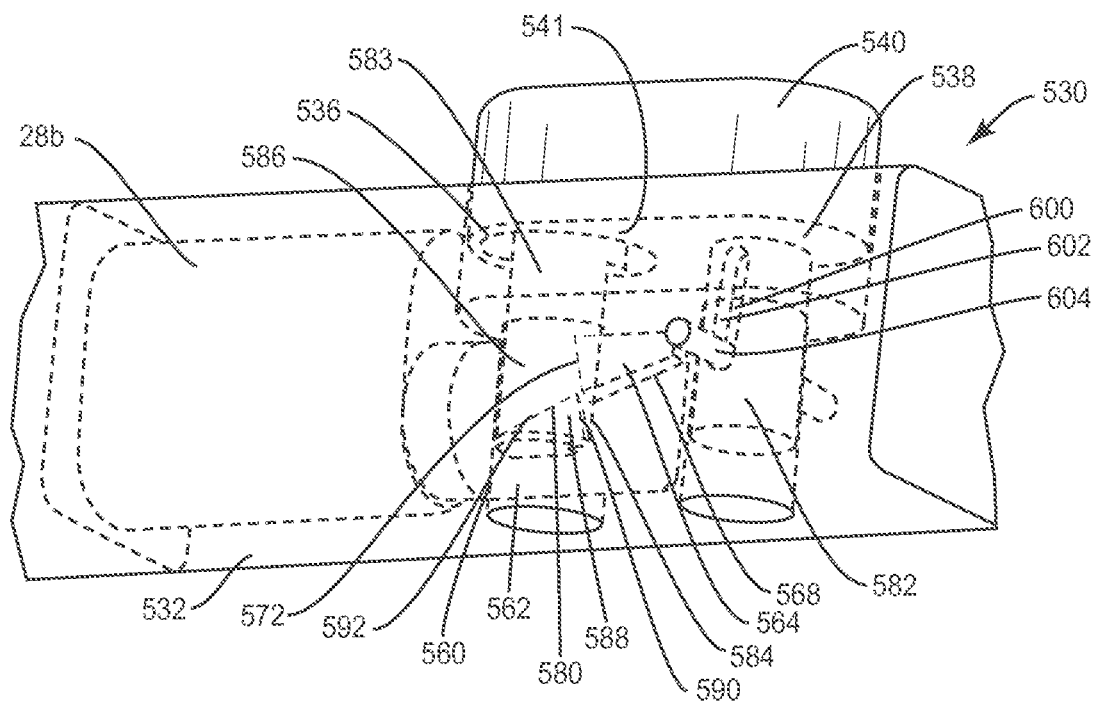
FIG. 12 is a cutaway view of the components shown in FIG. 11.

In one embodiment, as shown in FIGS. 11 and 12, surgical system 10, similar to the systems and methods described herein, includes an adaptor 530, similar to adaptor 330 described herein, for attaching a member, such as, for example, arm 20 described herein, with a part, such as, for example, blade 28 that includes an arm 28*b*, similar to arm 28*a*, having an oval cross section configuration.

Adaptor 530 includes a housing 532. Housing 532 is configured for a mating engagement with extension 24 of arm 20, as described herein. Housing 532 defines a cavity 536 and a cavity 538 for disposal of a push button 540, similar to button 340 described herein. Housing 532 defines a recess 544 for disposal of a portion of button 340 in an open and/or release position, as described herein.

Housing 532 includes surface 534 that defines a cavity 550 disposed transverse to cavities 536, 538. Cavity 550 is in communication with cavity 536 to facilitate translation of arm 28*b* within and relative to adaptor 530 to dispose blade 28 with arm 20 between a non-locked position and a locked position. Cavity 550 has an oval cross section configuration. Arm 28*b* is configured for disposal within cavity 550 such that surface 534 engages a surface of arm 28*b* in an interference fit to resist and/or prevent rotation of arm 28*b* relative to extension 24.

Button 540 is manipulable via engagement with arm 28*b* and/or depressible by a practitioner for translation to dispose blade 28 with arm 20 between the non-locked position and the locked position. Arm 28*b* includes a surface 560 that defines a channel 562. Surface 560 includes a wedge 564 disposed with channel 562. Wedge 564 includes a lead ramp 568. Wedge 564 includes a locking ramp 572. Ramps 568, 572 are configured for engagement with a wedge 588, as described herein, to facilitate translation and/or locking of blade 28 with arm 20, as described herein.

Button 540 includes a surface 541. An extension 580 and an extension 582 extend from surface 541 into housing 532. Extension 580 is configured for disposal within cavity 536. Extension 580 includes a cylindrical portion 583. Extension 580 includes a surface 584 that defines a channel 586. Surface 584 includes a wedge 588 disposed with channel 586 and configured for engagement with wedge 564, as described herein. Wedge 588 defines a ramp 592. Wedge 588 defines a ramp 596. Ramps 592, 596 form an apex. Ramp 568 is configured for slidable engagement with ramp 592 over the apex to engage ramp 596 to move button 540 between a locked position and an open position, similar to that described herein. Ramp 572 is configured for slidable engagement with ramp 596 such that adaptor 530 releasably locks blade 28 with arm 20. Extension 582 includes a surface 600 that defines a cavity 602. Cavity 602 is configured for disposal of an alignment pin 604.

Figure 13:
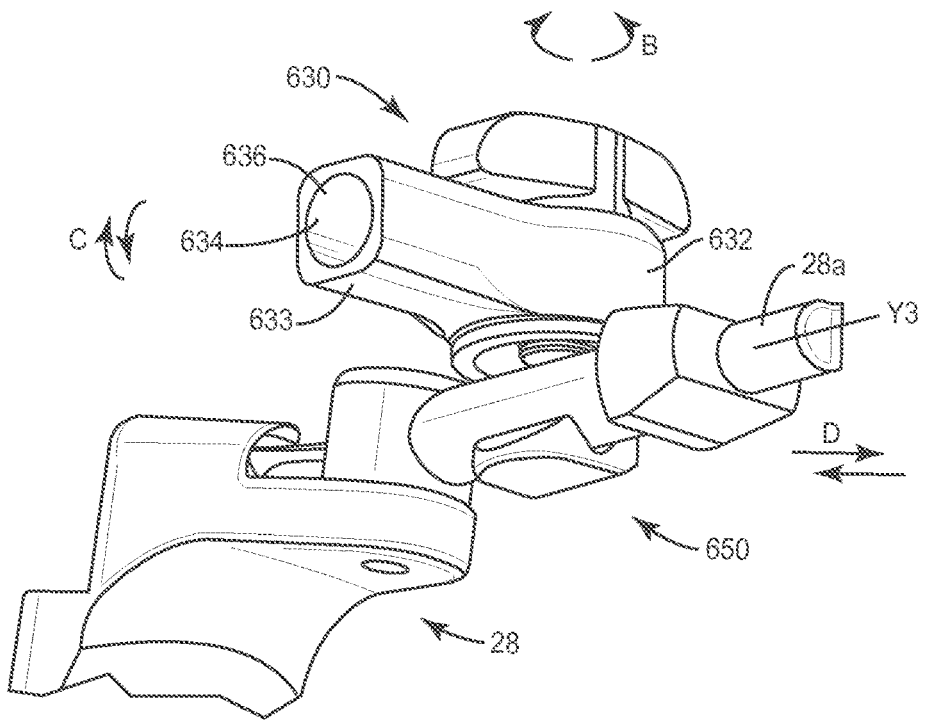
FIG. 13 is a break away perspective view of components of one embodiment of a surgical system in accordance with the principles of the present disclosure.
Figure 14:
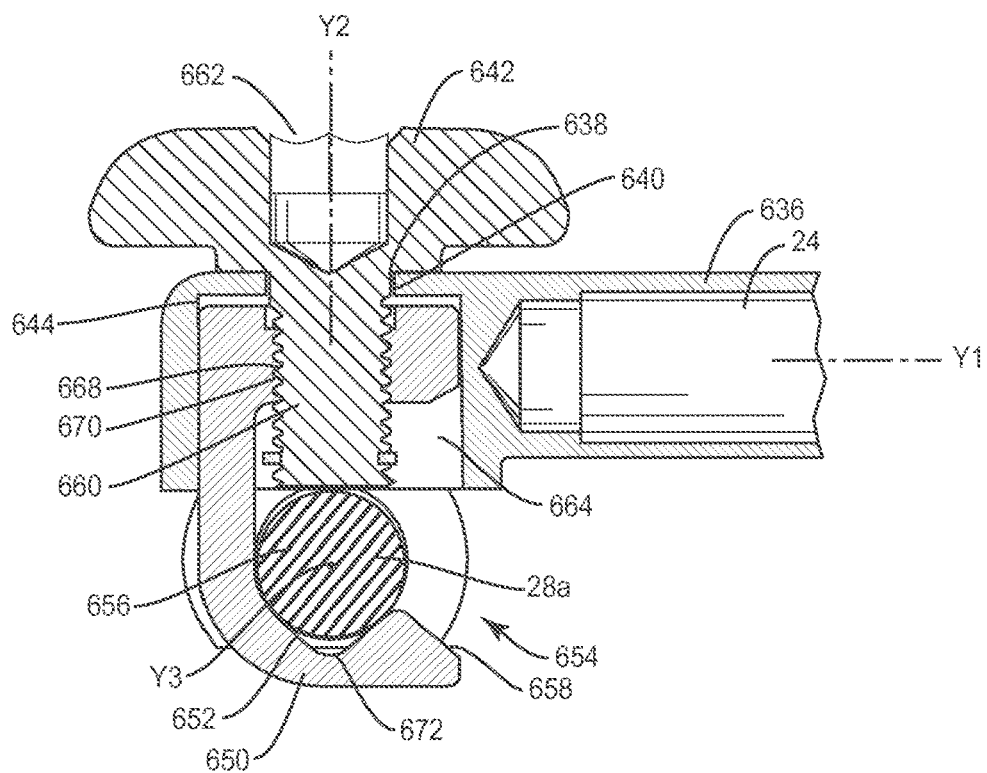
FIG. 14 is a cross section view of the components shown in FIG. 13.
Figure 15:
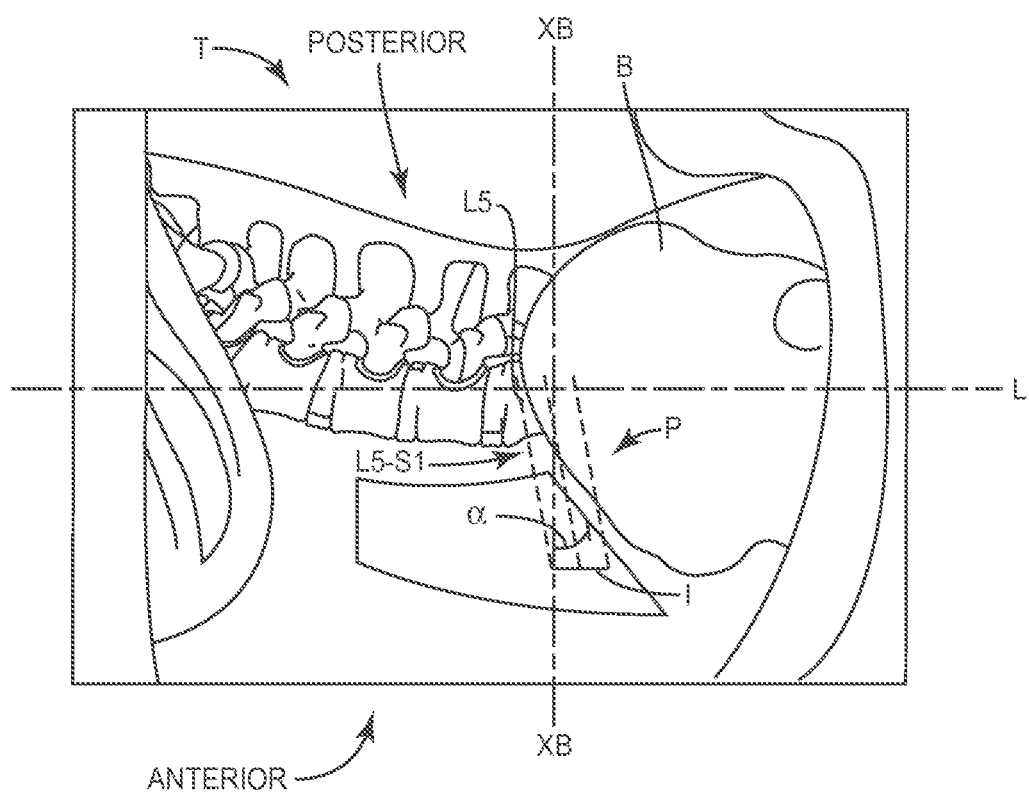
FIG. 15 is a plan view of components of one embodiment of a surgical system in accordance with the principles of the present disclosure disposed with a subject body.

In some embodiments, as shown in FIGS. 13 and 14, surgical system 10 includes an adaptor 630 configured for attaching a member, such as, for example, arm 20 described herein, with a part, such as, for example, blade 28. In some embodiments, adaptor 630 can be employed with one or more of arms 20, 60, 90 and blades 28, 68, 98, as described herein. In some embodiments, adaptor 630 includes a portion of an arm of a blade, such as, for example, arm 28a and a portion of a member, such as, for example, extension 24. In some embodiments, adaptor 630 is connected with extension 24 and such connection comprises a spheroidal joint, similar to ball joint 46. In some embodiments, adaptor 630 comprises a separate component of surgical system 10 that is attached with arm 20 and blade 28.

Adaptor 630 connects arm 20 with blade 28 and facilitates relative movement of arm 28a and extension 24. In some embodiments, adaptor 630 connects arm 20 with blade 28 such that blade 28 is movable to one or a plurality of degrees of freedom, as described with regard to retractor 12 herein, to one or a plurality of orientations relative to rail 14, stationary surgical equipment and/or subject body B in connection with a surgical procedure. In some embodiments, adaptor 630 connects arm 20 with blade 28 such that blade 28 is movable to a plurality of degrees of freedom including two degrees of freedom in rotation and one degrees of freedom in translation, relative to extension 24. In some embodiments, adaptor 630 connects arm 20 with blade 28 such that blade 28 is independently and selectively moveable relative to arm 20 to facilitate positioning of blade 28, as described herein.

Adaptor 630 includes a collar 632. Collar 632 includes an extension 633 having a surface 634 defining an opening 636 configured for disposal of extension 24. Extension 633 defines an axis Y1. In some embodiments, surface 634 and a surface of extension 24 comprise a spheroidal joint, similar to ball joint 46.

Collar 632 includes a surface 638 that defines an opening 640 for disposal of a handle 642 having a threaded shaft 660. Handle 642 includes a socket 662 having a hexalobe geometry configured for disposal of a similarly shaped bit of a tool, such as, for example, a driver (not shown) to engage handle 642 to rotate shaft 660. In some embodiments, socket 662 has a cruciform, phillips, square, hexagonal, polygonal, star cross sectional configuration configured for disposal of a correspondingly shaped portion of a driver.

Collar 632 includes an inner surface 644 that defines a cavity 664 configured for disposal of a jaw 650. Jaw 650 includes an inner surface 668 that defines a threaded passageway 670 configured for disposal and threaded fixation with shaft 660. Jaw 650 is engageable with handle 642 in threaded fixation to dispose blade 28 with arm 20 between a non-locked position and a locked position. Shaft 660 is engaged with jaw 650 to define an axis Y2.

Jaw 650 includes a surface 652 that defines a cavity, such as, for example, a lateral passageway 654. Passageway 654 is configured for disposal of arm 28a, which define an axis Y3. Surface 652 includes a retaining flange 658. Flange 658 defines a recess 672 with surface 652 configured for disposal of arm 28a. In some embodiments, flange 658 is oriented in a snap fit configuration to retain arm 28a with adaptor 630. In some embodiments, adaptor 630 includes a spring (not shown) disposed within cavity 664 to bias adaptor 630 in a provisionally dosed or locked position with arm 28a to retain arm 28a with adaptor 630 prior to fixation of arm 20 in a final orientation. In some embodiments, the provisionally dosed or locked position includes jaw 650 being biased and/or drawn upwardly with arm 28a relative to cavity 664. In some embodiments, the spring (not shown) is disposed about shaft 660. In some embodiments, the spring (not shown) is disposed between jaw 650 and surface 644.

Adaptor 630 connects arm 20 with blade 28 such that blade 28 is movable to a plurality of degrees of freedom. Adaptor 630 is fixed with extension 24. Arm 28a is disposed with passageway 654. Adaptor 630 is spring preloaded to bias handle 642 and/or jaw 650 to a provisionally dosed or locked position with arm 28a to retain arm 28a with adaptor 630 prior to fixation of arm 20 in a final orientation.

Arm 28a is movable to at least three additional degrees of freedom as facilitated by adaptor 630 including two degrees of freedom in rotation and one degree of freedom in translation, relative to extension 24. Arm 28a is rotatable relative to and about axis Y2, in the direction shown by arrows B in FIG. 13, rotatable relative to and about axis Y3, in the direction shown by arrows C, and translatable relative to and along axis Y3, in the direction shown by arrows D, to a selected orientation relative to extension 24. Upon positioning of blade 28 relative to extension 24 in a selected orientation, as described herein, a driver is engaged with socket 662 and/or handle 642 is manipulated to rotate shaft 660 in threaded engagement with jaw 650. Shaft 660 engages arm 28a to lock blade 28 in the selected orientation with extension 24.

In assembly, operation and use, as shown in FIGS. 15-18, surgical system 10, similar to the systems described herein, is employed with a surgical procedure for treatment of a spinal disorder, such as those described herein, affecting a section of a spine of a patient. Surgical system 10 may also be employed with other surgical procedures. To treat the affected section of vertebrae V of a subject body B of a patient, body B is disposed in a side orientation relative to a surgical fixed surface, such as, for example, a surgical table configured for supporting body B. Body B is placed on a side, left side up. In some embodiments, this results in the vena cava being oriented on the right side of centerline. Body B is oriented such that the procedure can be performed obliquely in front of the iliac crest to provide direct access to L5-S1 intervertebral space along surgical pathway P, described herein, while avoiding selected muscular and abdominal anatomical structures. In some embodiments, placement of body B on its side facilitates access to surgical pathway P that is disposed at oblique angle α relative to axis XB.

Figure 16:
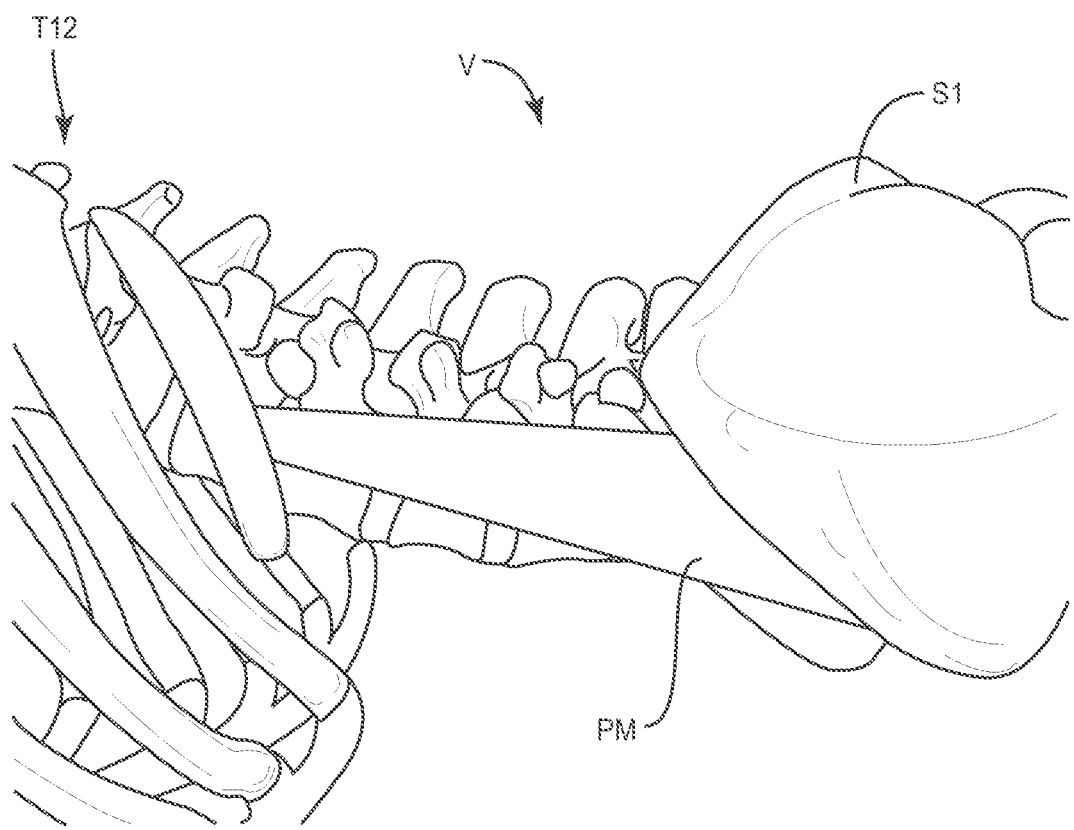
FIG. 16 is a plan view of components of one embodiment of a surgical system in accordance with the principles of the present disclosure disposed with a subject body.
Figure 17:
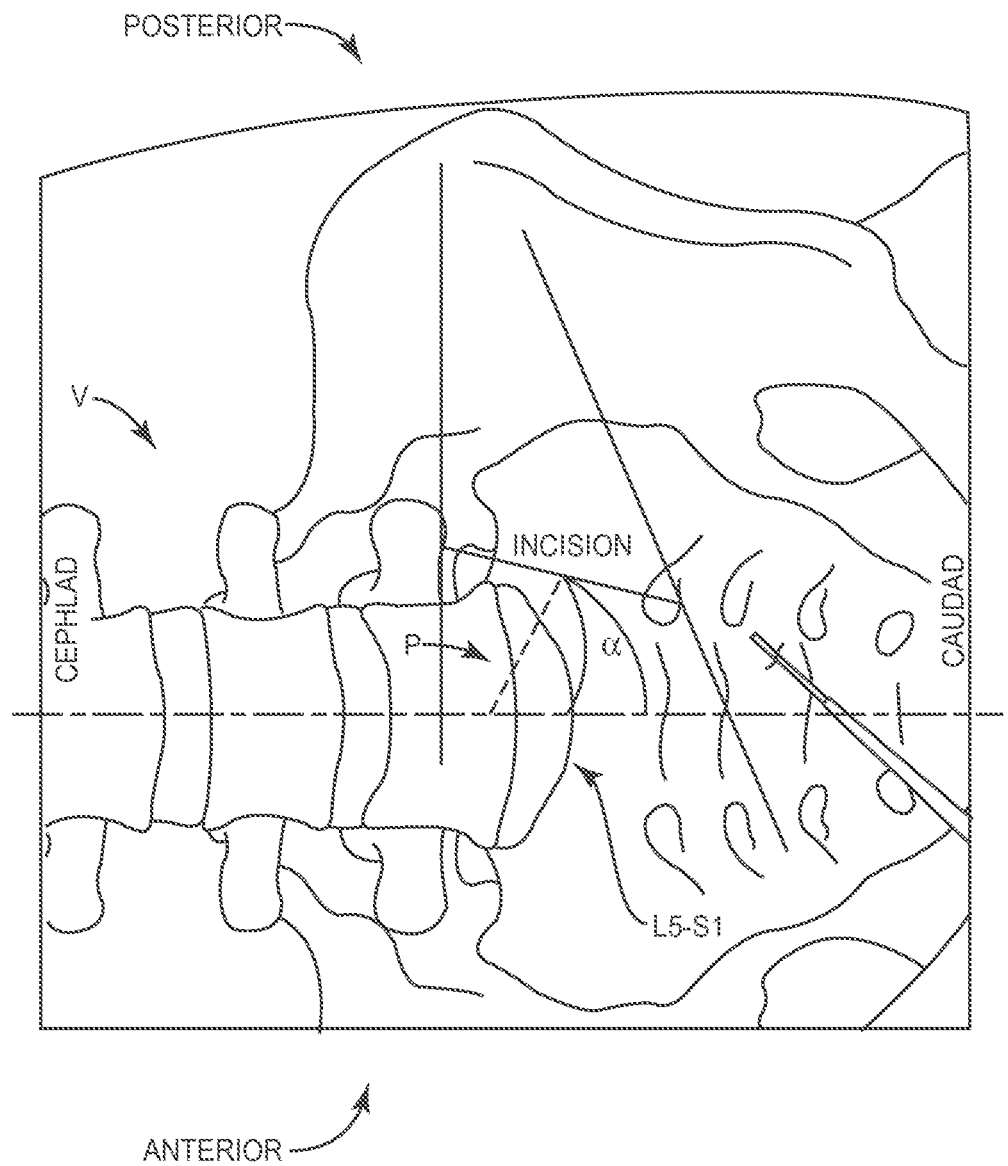
FIG. 17 is a plan view of components of one embodiment of a surgical system in accordance with the principles of the present disclosure disposed with a subject body.

For example, as shown in FIG. 16, lateral anatomy from T12 to S1 shows a retroperitoneal corridor that is formed by bony anatomy of the ribs and pelvis and psoas muscle PM underneath. From T12-L2, an exemplary approach for access to surgical pathway P may be a direct lateral approach to avoid the ribs ventrally. Psoas muscle PM at these levels may be smaller and less innervated and thus can be retracted or dilated. The L2 to L4 region is generally beneath or caudal to the ribs with psoas muscle PM transitioning more anteriorly, such that a more oblique anterior approach to avoid violation or minimize retraction may be employed. In some embodiments, the pelvis restricts lateral access in the L4-L5 region, with the psoas transitioning even further anterior, moving an exemplary approach for access to surgical pathway P anteriorly. In the L5-S1 region, due to bifurcation of the great vessels laterally, safe access to the L5-S1 disc space is a more anterior approach to surgical pathway P, which can be accomplished at an oblique angle with the patient in the lateral position, as described herein.

A marking is drawn from the anterior of body B to the posterior of body B to identify the slope and lordosis of the L5-S1 intervertebral space and the line is continued along the same trajectory as the slope onto the abdomen for accessing surgical pathway P. The amount of slope visually indicates the most caudal, toward the coccyx, aspect of the incision to enter the lordosis of the L5-S1 intervertebral space with respect to the cephalad, towards the head. A second line is drawn from the center of the disc and projecting perpendicular to the floor onto the abdomen. This line represents the actual level of the disc in the abdomen. An incision I is made with a surgical instrument, such as, for example, a scalpel, for substantial alignment and communication to create surgical pathway P from posterio-rostral to antero-caudal medial approximately 1-2 finger breaths from the ASIS and pelvis, between the two lines. In some embodiments, the incision can extend to higher levels of the spine and distally to the symphisis pubis. In one embodiment, a separate L5-S1 incision is utilized at a site lower and more anterior than the L4-L5.

In some embodiments, the external oblique muscle or the aponeurosis and fascia are encountered upon entry into incision I. In some embodiments, the retroperitoneal dissection and exposure is accomplished by utilizing a blunt finger to facilitate a wider exposure for a retractor, as described herein. In some embodiments, the ureter is exposed and dissection of a wide rostral to caudal development of the retroperitoneal plane is utilized to protect the ureter, thereby maintaining its attachment to the posterior peritoneum while mobilizing anteriorly.

In some embodiments, surgical pathway P is created with the progression of the two finger dissection down the pelvis and across the psoas continues anteriorly from the pelvis to locate the iliac artery pulse. In some embodiments, the finger dissection is continued past the pulsating iliac artery medial to the artery on the sacral promontory and the L5-S1 intervertebral space. In some embodiments, lighted retractors are placed sequentially down onto the anterior spine and the adventitial layers that are on the anterior disc and sacrum are encountered.

In some embodiments, the oblique approach creating surgical pathway P accesses the L5-S1 intervertebral space below the bifurcation, as such, the ilio-lumbar vein is not ligated since posterior retraction of the left common iliac vein and artery laterally does not cause stretch and potential avulsion.

A surgical instrument, such as, for example, retractor 12, as described herein, is disposed with incision I and in communication with surgical pathway P for spacing tissue. Retractor blades 28, 68, 98, as described herein, are configured for insertion sequentially around the L5-S1 intervertebral space to protect tissue and/or vessels, as described herein. Rail 14 is attached to surgical equipment, as described herein. In some embodiments, an adaptor, such as, for example, adaptor 630 is attached with arms 20, 60 and/or 90 and blades 28, 68 and/or 98, as shown in FIG. 18, similar to that described herein.

Adaptor 630 connects blade 28 with arm 20, as described herein, such that blade 28 is movable in a plurality of degrees of freedom to one or a plurality of orientations, relative to rail 14, arm 20, stationary surgical equipment and/or tissue of subject body B adjacent the surgical site in connection with a surgical procedure. Blade 28 is manipulated for movement, as described herein, via adaptor 630 and/or arm 20 relative to incision I to align and guide blade 28 into a posterior orientation and/or engagement with a posterior portion of incision I relative to body B.

Adaptor 630 connects blade 68 with arm 60, as described herein, such that blade 68 is movable in a plurality of degrees of freedom to one or a plurality of orientations, relative to rail 14, arm 60, stationary surgical equipment and/or tissue of subject body B adjacent the surgical site in connection with a surgical procedure. Blade 68 is manipulated for movement, as described herein, via adaptor 630 and/or arm 60 relative to incision I to align and guide blade 68 into an anterior orientation and/or engagement with an anterior portion of incision I relative to body B.

Adaptor 630 connects blade 98 with arm 90, as described herein, such that blade 98 is movable in a plurality of degrees of freedom to one or a plurality of orientations, relative to rail 14, arm 90, stationary surgical equipment and/or tissue of subject body B adjacent the surgical site in connection with a surgical procedure. Blade 98 is manipulated for movement, as described herein, via adaptor 630 and/or arm 90 relative to incision I to align and guide blade 98 into a cephalad orientation and/or engagement with a cephalad portion of incision I relative to body B. Retractor 12 spaces tissue adjacent incision I to define surgical pathway P, which allows for instruments and/or implants to be inserted into body B obliquely through surgical pathway P.

In some embodiments, a discectomy is performed via surgical pathway P. In some embodiments, instruments, such as, for example, a Cobb elevator, mallet, shaver, serrated curettes, rasp, a ring curette, a uterine curette and/or a combination thereof are utilized to perform a discectomy of the disc space.

In some embodiments, an anterior longitudinal ligament (ALL) release procedure can be performed using an OLIF approach post-discectomy. For example, loosening the ALL can be performed by placing holes or partial cuts in the ALL such that the OLIF surgical pathway is immediately closer to the ALL.

In some embodiments, trial implants (not shown) are delivered along surgical pathway P. The trial implants are used to distract one or more intervertebral spaces of the L2-L5 vertebral levels and apply appropriate tension in the intervertebral space allowing for indirect decompression. In one embodiment, a direct decompression of the disc space is performed by removing a portion of a herniated disc. In some embodiments, one or a plurality of interbody implants can be introduced and delivered along surgical pathway P for implantation with one or more intervertebral spaces of the L2-L5 vertebral levels.

In some embodiments, pilot holes or the like are made in the vertebrae adjacent its intervertebral space, via surgical pathway P for receiving bone fasteners and/or attaching spinal constructs, which may include rods and plates. An inserter is attached with the implants and/or spinal constructs for delivery along surgical pathway P adjacent to a surgical site for implantation adjacent one or more vertebra and/or intervertebral spaces of the L2-L5 vertebral levels.

Upon completion of a procedure, as described herein, the surgical instruments, assemblies and non-implanted components of surgical system 10 are removed and the incision(s) are dosed. One or more of the components of surgical system 10 can be made of radiolucent materials such as polymers. Radiopaque markers may be included for identification under x-ray, fluoroscopy, CT or other imaging techniques. In some embodiments, the use of surgical navigation, micro-surgical and image guided technologies may be employed to access, view and repair spinal deterioration or damage, with the aid of surgical system 10. In some embodiments, surgical system 10 may include one or a plurality of plates, connectors and/or bone fasteners for use with a single vertebral level or a plurality of vertebral levels.

In one embodiment, surgical system 10 includes an agent, which may be disposed, packed, coated or layered within, on or about the components and/or surfaces of surgical system 10. In some embodiments, the agent may include bone growth promoting material, such as, for example, bone graft to enhance fixation of the components and/or surfaces of surgical system 10 with vertebrae. In some embodiments, the agent may include one or a plurality of therapeutic agents and/or pharmacological agents for release, including sustained release, to treat, for example, pain, inflammation and degeneration.

Figure 19:
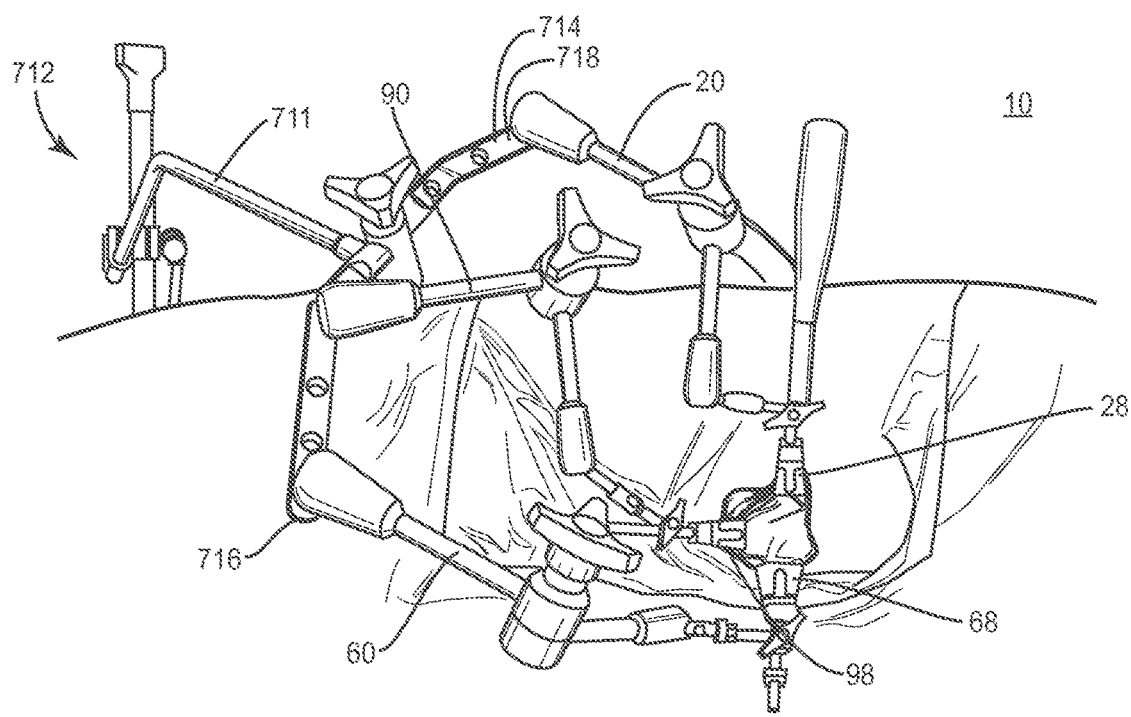
FIG. 19 is a plan view of components of one embodiment of a surgical system in accordance with the principles of the present disclosure disposed with a subject body.
Figure 20:
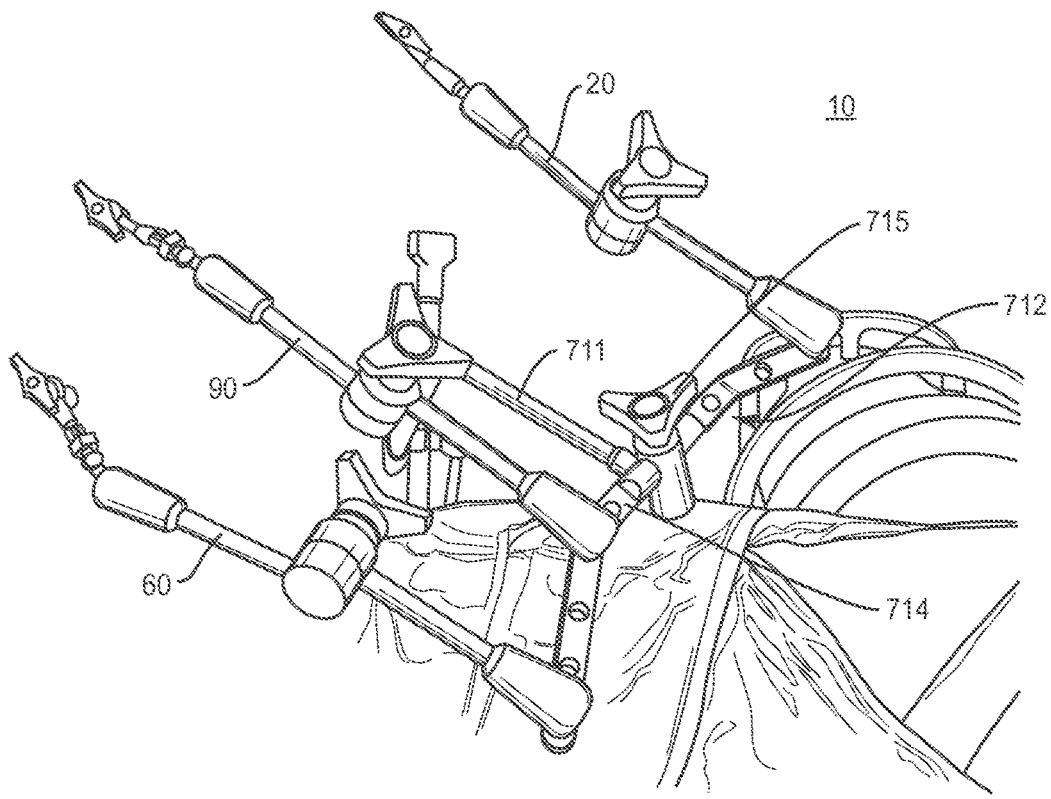
FIG. 20 is a perspective view of components of one embodiment of a surgical system in accordance with the principles of the present disclosure disposed with a subject body.

In one embodiment, as shown in FIGS. 19 and 20, surgical system 10, similar to the systems and methods described herein, comprises a surgical instrument, such as, for example, a surgical retractor 712, similar to surgical retractor 12 described herein. Surgical retractor 712 includes a rail 714, similar to rail 14 described herein, configured for connection with an arm 711 of a surgical table (not shown). Rail 714 is configured to facilitate placement and/or orientation of surgical retractor 712 relative to subject body B and/or an incision in connection with a surgical procedure.

Rail 714 extends between an end 716 and an end 718. Rail 714 extends in an arcuate configuration between ends 716, 718. In some embodiments, rail 714 is movable relative to arm 711 and is lockable with arm 711 in a selected position and/or orientation. In some embodiments, rail 714 includes a knob 715, similar to knob 15 described herein, which locks rail 714 with arm 711 in a selected position and/or orientation relative to the surgical table and/or a patient body, as described herein.

Retractor arms 20, 60, 90, as described herein, are attached with rail 714 such that one or a plurality of arms 20, 60, 90 are movable in one or a plurality of degrees of freedom to one or a plurality of orientations, similar to that described herein, relative to rail 714, stationary surgical equipment and/or subject body B in connection with a surgical procedure. The configuration of surgical retractor 712 provides arms 20, 60, 90, which are independently and selectively movable relative to rail 714, stationary surgical equipment and/or subject body B for connection to blades 28, 68, 98, as described herein, that can be disposed at a selected angle of trajectory and unconstrained by placement of adjacent blades.

Figure 21:
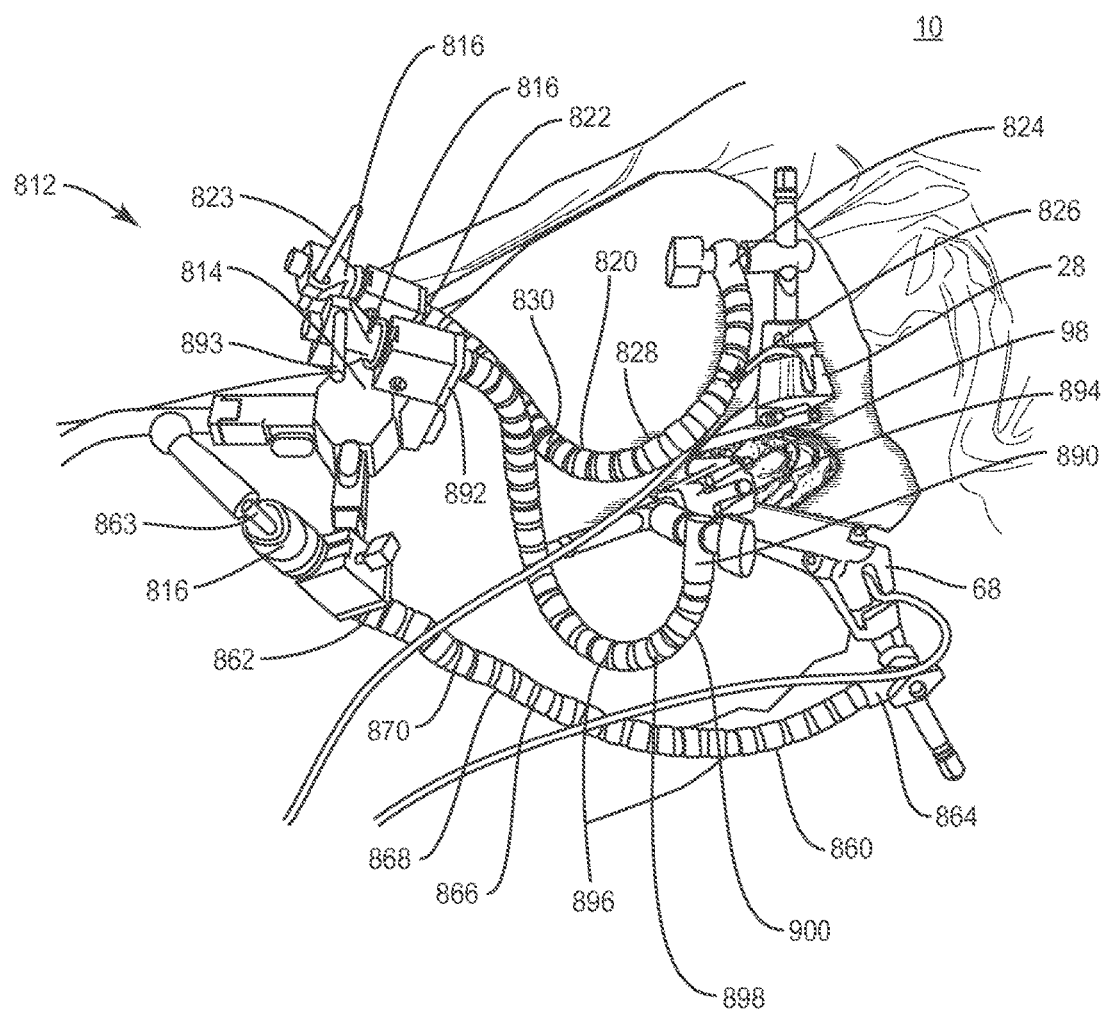
FIG. 21 is a perspective view of components of one embodiment of a surgical system in accordance with the principles of the present disclosure disposed with a subject body.

In one embodiment, as shown in FIG. 21, surgical system 10, similar to the systems and methods described herein, comprises a surgical instrument, such as, for example, a retractor 812, similar to retractor 12 described herein. Retractor 812 includes an element, such as, for example, a hub 814. Hub 814 is configured for connection with a fixture, such as, for example, stationary surgical equipment, such as, for example, a surgical table (not shown). Hub 814 includes cavities 816 configured for connection with members, such as, for example, segmental articulating arms 820, 860, 890, as described herein.

Arm 820 extends between an end 822 and an end 824. Arm 820 includes a segmented articulating configuration, such as, for example, a link configuration 826. Link configuration 826 includes a series of interconnected links 828, which are relatively movable. End 822 includes a handle 823 having a chain link (not shown) extending therefrom. The chain link extends through links 828 and is fixed with end 824. Link configuration 826 is disposable between a flexible orientation to facilitate articulation and a relatively rigid orientation to facilitate orientation of blade 28, as described herein, to engage and space apart tissue at a surgical site, similar to that described herein. Each link 828 has an outer surface 830. In some embodiments, all or only a portion of each outer surface 830 may have alternate surface configurations, such as, for example, rough, undulating, porous, semi-porous, dimpled, polished and/or textured.

In the first orientation, link configuration 826 is disposed in a relatively flexible configuration such that links 828 are relatively movable. Arm 820 is manipulated and articulated into a selected orientation, which may include linear, non-linear, arcuate, angled, offset and/or staggered. Handle 823 is rotated to draw and tension the chain link for disposing arm 820 in a second or fixed orientation to engage and space apart tissue at a surgical site.

Arm 820 is connected with hub 814. Arm 820 is configured for independent and selective movement relative to hub 814. Arm 820 is connected with posterior blade 28, as described herein. Blade 28 is configured for disposal in a posterior orientation and engageable with tissue of a substantially posterior portion of an incision relative to a body, as described herein. Blade 28 is disposable in a configuration to space tissue of the incision to define an oblique surgical pathway P relative to a bilateral axis of the body, as described herein.

Arm 860 extends between an end 862 and an end 864. Arm 860 includes a segmented articulating configuration, such as, for example, a link configuration 866. Link configuration 866 includes a series of interconnected links 868, which are relatively movable. End 862 includes a handle 863 having a chain link (not shown) extending therefrom. The chain link extends through links 868 and is fixed with end 864. Link configuration 866 is disposable between a flexible orientation to facilitate articulation and a relatively rigid orientation to facilitate orientation of blade 68, as described herein, to engage and space apart tissue at a surgical site, similar to that described herein. Each link 868 has an outer surface 870. In some embodiments, all or only a portion of each outer surface 870 may have alternate surface configurations, such as, for example, rough, undulating, porous, semi-porous, dimpled, polished and/or textured.

In the first orientation, link configuration 866 is disposed in a relatively flexible configuration such that links 868 are relatively movable. Arm 860 is manipulated and articulated into a selected orientation, which may include linear, non-linear, arcuate, angled, offset and/or staggered. Handle 863 is rotated to draw and tension the chain link for disposing arm 860 in a second or fixed orientation to engage and space apart tissue at a surgical site.

Arm 860 is connected with hub 814. Arm 860 is configured for independent and selective movement relative to hub 814. Arm 860 is connected with anterior blade 68, as described herein. Blade 68 is configured for disposal in an anterior orientation and engageable with tissue of a substantially anterior portion of an incision relative to a body, as described herein. Blade 68 is disposable in a configuration to space tissue of the incision to define an oblique surgical pathway P relative to a bilateral axis of the body, as described herein.

Arm 890 extends between an end 892 and an end 894. Arm 890 includes a segmented articulating configuration, such as, for example, a link configuration 896. Link configuration 896 includes a series of interconnected links 898, which are relatively movable. End 892 includes a handle 893 having a chain link (not shown) extending therefrom. The chain link extends through links 898 and is fixed with end 894. Link configuration 896 is disposable between a flexible orientation to facilitate articulation and a relatively rigid orientation to facilitate orientation of blade 98, as described herein, to engage and space apart tissue at a surgical site, similar to that described herein. Each link 898 has an outer surface 900. In some embodiments, all or only a portion of each outer surface 900 may have alternate surface configurations, such as, for example, rough, undulating, porous, semi-porous, dimpled, polished and/or textured.

In the first orientation, link configuration 896 is disposed in a relatively flexible configuration such that links 898 are relatively movable. Arm 890 is manipulated and articulated into a selected orientation, which may include linear, non-linear, arcuate, angled, offset and/or staggered. Handle 893 is rotated to draw and tension the chain link for disposing arm 890 in a second or fixed orientation to engage and space apart tissue at a surgical site.

Arm 890 is connected with hub 814. Arm 890 is configured for independent and selective movement relative to hub 814. Arm 890 is connected with cephalad blade 98, as described herein. Blade 98 is configured for disposal in a cephalad orientation and engageable with tissue of a substantially cephalad portion of an incision relative to a body, as described herein. Blade 98 is disposable in a configuration to space tissue of the incision to define an oblique surgical pathway P relative to a bilateral axis of the body, as described herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument assembly comprising:
   an element connectable with a fixture and comprising a shaft having a linear portion and spaced apart first, second and third projections that each extend directly from an outer surface of the linear portion wherein the projections are each fixed relative to the shaft, each projection defining an axis, the axes extending parallel to one another;
   a first member comprising a collar that directly engages the first projection such that the first member is independently and selectively movable relative to the element, the first member including a part engageable with tissue of a substantially posterior portion of an incision relative to a body;
   a second member comprising a collar that directly engages the second projection such that the second member is independently and selectively movable relative to the element, the second member including a part engageable with tissue of a substantially anterior portion of the incision relative to the body; and
   a third member comprising a collar that directly engages the third projection such that the third member is independently and selectively movable relative to the element, the third member including a part engageable with tissue of a substantially cephalad portion of the incision relative to the body.

2. A surgical instrument assembly as recited in claim 1, wherein at least one of the members includes a first extension and a second extension.

3. A surgical instrument assembly as recited in claim 2, wherein at least one of the extensions is selectively rotatable relative to the element.

4. A surgical instrument assembly as recited in claim 2, wherein the second extension is selectively rotatable relative to the first extension.

5. A surgical instrument assembly as recited in claim 1, wherein at least one of the members includes a spheroidal joint connection with the element.

6. A surgical instrument assembly as recited in claim 1, wherein at least one of the members includes an adaptor disposed between the member and the part, the adaptor including a ramp interface such that the part is releasably engageable with the member.

7. A surgical instrument assembly as recited in claim 6, wherein the adaptor includes a quick release connection including a push button release.

8. A surgical instrument assembly as recited in claim 1, wherein one of the parts includes a posterior blade.

9. A surgical instrument assembly as recited in claim 1, wherein one of the parts includes an anterior blade.

10. A surgical instrument assembly as recited in claim 1, wherein one of the parts includes a cephalad blade.

11. A surgical instrument assembly as recited in claim 1, wherein the parts are disposable in a configuration to space tissue of an incision to define an oblique surgical pathway relative to a bilateral axis of a body.

12. A surgical instrument assembly as recited in claim 1, wherein the shaft comprises a linear configuration.

13. A surgical instrument assembly as recited in claim 1, wherein the projections each define a ball and the collars each define a socket having one of the balls disposed therein to form a ball and socket joint.

14. A surgical instrument assembly as recited in claim 1, wherein the part of the first member is a retractor blade, the first member including a clamp disposed between the collar of the first member and the retractor blade, the clamp comprising a cavity and a jaw, the law being configured for translation within the cavity to engage the retractor blade to fix the retractor blade with the clamp.

15. A surgical instrument assembly comprising:
    an element connectable with a fixture and comprising a shaft having a linear portion, the linear portion spaced apart first, second and third projections that each extend directly from an outer surface of the linear portion wherein the projections are each fixed relative to the shaft, the projections each defining an axis, the axes each extending parallel to one another;
    a first arm comprising a collar that directly engages the first projection such that the first arm is independently and selectively movable relative to the element, the first arm including a posterior blade;
    a second arm comprising a collar that directly engages the first projection such that the second arm is independently and selectively movable relative to the element, the second arm including an anterior blade; and
    a third arm comprising a collar that directly engages the first projection such that the third arm is independently and selectively movable relative to the element, the third arm including a cephalad blade,
    wherein the arms are disposable in a configuration to space tissue of an incision to define an oblique surgical pathway relative to a bilateral axis of a body.

16. A surgical instrument assembly as recited in claim 15, wherein at least one of the arms includes a first extension and a second extension.

17. A surgical instrument assembly as recited in claim 16, wherein at least one of the extensions is selectively rotatable and/or translatable relative to the element.

18. A surgical instrument assembly as recited in claim 15, wherein at least one of the arms includes an adaptor disposed between the arm and the blade such that the blade is releasably engageable with the arm.

19. A surgical instrument assembly comprising:
an element connectable with a fixture and comprising a shaft and spaced apart first, second and third projections that each extend outwardly from an outer surface of the shaft;
a first member comprising a collar that directly engages the first projection such that the first member is independently and selectively movable relative to the element, the first member including a part engageable with tissue of a substantially posterior portion of an incision relative to a body;
a second member comprising a collar that directly engages the second projection such that the second member is independently and selectively movable relative to the element, the second member including a part engageable with tissue of a substantially anterior portion of the incision relative to the body; and
a third member comprising a collar that directly engages the third projection such that the third member is independently and selectively movable relative to the element, the third member including a part engageable with tissue of a substantially cephalad portion of the incision relative to the body,
wherein the part of the first member is a retractor blade, the first member including an adaptor disposed between the collar of the first member and the retractor blade,
wherein the retractor blade comprises a cylinder including a first wedge disposed within a channel of the cylinder,
wherein the adaptor comprises a housing having a cavity configured for disposal of the cylinder, the adaptor comprising a push button having an extension comprising a second wedge disposed in a channel of the extension, the extension being configured for disposal in an axial cavity of the housing, and
wherein the push button is inserted into the housing such that the wedges move from a first orientation in which the second wedge is movable relative to the first wedge and the retractor arm is removable from the adaptor and a second orientation in which the second wedge is engaged with the first wedge in an interference fit to prevent the retractor arm from disengaging the adaptor.

20. A surgical instrument assembly as recited in claim 19, wherein the first wedge is fixed relative to the cylinder.

* * * * *

UNITED STATES PATENT AND TRADEMARK OFFICE
CERTIFICATE OF CORRECTION

Page 1 of 1

PATENT NO. : 10,219,798 B2
APPLICATION NO. : 14/800302
DATED : March 5, 2019
INVENTOR(S) : Cristian A. Capote It is certified that error appears in the above-identified patent and that said Letters Patent is hereby corrected as shown below:

In the Specification

Column 6, Line 3, delete "dearly" and insert -- clearly --, therefor.

Column 7, Line 24, delete "bioompatible" and insert -- biocompatible --, therefor.

Column 9, Line 62, delete "damp 50" and insert -- clamp 50 --, therefor.

Column 10, Lines 2-3, delete "damp 50" and insert -- clamp 50 --, therefor.

Column 10, Line 8, delete "damp 50." and insert -- clamp 50. --, therefor.

Column 11, Line 28, delete "damp 88" and insert -- clamp 88 --, therefor.

Column 11, Lines 35-36, delete "damp 88" and insert -- clamp 88 --, therefor.

Column 11, Line 41, delete "damp 88." and insert -- clamp 88. --, therefor.

Column 12, Line 61, delete "damp 118" and insert -- clamp 118 --, therefor.

Column 13, Line 2, delete "damp 118" and insert -- clamp 118 --, therefor.

Column 13, Line 7, delete "damp 88." and insert -- clamp 88. --, therefor.

Column 18, Line 4, delete "dosed" and insert -- closed --, therefor.

In the Claims

Column 24, Line 32, Claim 14, delete "law" and insert -- jaw --, therefor.

Signed and Sealed this
Sixteenth Day of July, 2019

Andrei Iancu
*Director of the United States Patent and Trademark Office*